(12) United States Patent
Nicolaou et al.

(10) Patent No.: US 8,003,801 B2
(45) Date of Patent: *Aug. 23, 2011

(54) CHEMICAL SYNTHESIS OF A HIGHLY POTENT EPOTHILONE

(75) Inventors: Kyriacos C. Nicolaou, La Jolla, CA (US); Benjamin Pratt, San Diego, CA (US); Stellios Arseniyadis, Paris (FR)

(73) Assignee: The Scripps Research Institute, LaJolla, CA (US)

( * ) Notice: Subject to any disclaimer, the term of this patent is extended or adjusted under 35 U.S.C. 154(b) by 273 days.

This patent is subject to a terminal disclaimer.

(21) Appl. No.: 12/092,038

(22) PCT Filed: Nov. 9, 2006

(86) PCT No.: PCT/US2006/060710
§ 371 (c)(1), (2), (4) Date: Apr. 29, 2008

(87) PCT Pub. No.: WO2007/062288
PCT Pub. Date: May 31, 2007

(65) Prior Publication Data
US 2008/0293747 A1    Nov. 27, 2008

Related U.S. Application Data

(60) Provisional application No. 60/739,816, filed on Nov. 22, 2005.

(51) Int. Cl.
C07D 277/04 (2006.01)
C07D 277/60 (2006.01)
C07D 257/04 (2006.01)
C07D 231/00 (2006.01)
C07D 233/00 (2006.01)
C07D 249/08 (2006.01)

(52) U.S. Cl. ..... 548/146; 548/250; 548/148; 548/356.1; 548/262.2; 548/300.1

(58) Field of Classification Search ............... 548/250, 548/146, 148, 356.1, 262.2, 300.1
See application file for complete search history.

(56) References Cited

U.S. PATENT DOCUMENTS 6,380,394 B1 * 4/2002 Nicolaou et al. .......... 548/125
6,441,186 B1   8/2002 Nicolaou et al.
6,531,497 B1   3/2003 Nicolaou et al.
6,660,758 B1  12/2003 Nicolaou et al.
6,780,620 B1   8/2004 Li et al.
7,169,930 B2 * 1/2007 Nicolaou et al. .......... 548/182
7,173,137 B2 * 2/2007 Nicolaou et al. .......... 546/209
7,358,266 B2   4/2008 Nicolaou et al.
7,579,366 B2 * 8/2009 Nicolaou et al. .......... 514/342

FOREIGN PATENT DOCUMENTS

WO     WO 99/67252    * 12/1999

OTHER PUBLICATIONS

Nicolaou et al. J Am.Chem.Soc., 123, 2001., 9313-9323.*
Altman et. al. Merger of Natural product synthesis and medicinal chemistry, Org. Biol. Chem. 2004, 2, 2137-2152.*
ISR of WO 2007/062288 published on May 31, 2007.
Written Opinion of WO 2007/062288 published on May 31, 2007.
Nicolaou et al., ChemMedChem 2006, 1, 41-44.
Höfle et al., Angew. Chem. 1996, 108, 1671-1673; Angew. Chem. Int. Ed. 1996, 35, 1567-1569.
Altmann, Org. Biomol. Chem. 2004, 2, 2137-2152.
Watkins et al., Curr. Pharm. Design 2005, 11, 1615-1653.
Nicolaou et al., Chem. Commun. 2001, 1523-1535.
Nicolaou et al., Pure Appl. Chem. 1999, 71, 989-997.
Harris et al., J. Org. Chem. 1999, 64, 8434-8456.
Nicolaou et al., Angew. Chem. 1998, 110, 2120-2153; Angew. Chem. Int. Ed. 1998, 37, 2014-2045.
Okuno et al., J. Clin. Oncol. 2005, 23, 3069-3073.
Altmann, Curr. Pharm. Design 2005, 11, 1595-1613.
Rivkin et al.,, Angew. Chem. 2005, 117, 2898-2910; Angew. Chem. Int. Ed. 2005, 44,2838-2850.
Kolman, Curr. Opin. Invest. Drugs 2004, 5,1292-1297.
Kolman, Curr. Opin. Invest. Drugs 2004, 5,657-667.
Galmarini et al., iDrugs 2003, 6,1182-1187.
Biswas et al., J. Am. Chem. Soc. 2002, 124, 9825-9832.
Buey et al., Chem. Biol. 2004, 11, 225-236.
Nicolaou et al., Angew. Chem. 2003, 115, 3639-3644; Angew. Chem., Int. Ed. 2003, 42,3515-3520.
Nicolaou et al., Tetrahedron 2002, 58,6413-6432.
Nicolau et al., J. Am. Chem. Soc. 2001, 123, 9313-9323.
Nicolaou et al., Chem. Biol. 2000, 7, 593-599.
Nettles et al., Science 2004, 305, 866-869.
Heinz et al., Angew. Chem. 2005, 117, 1324-1327; Angew. Chem. Int. Ed. 2005, 44, 1298-1301.
Sakamoto et al., Heterocycles 1992, 33, 813-818.
Kato et al., J. Org. Chem. 1997, 62, 6833-6841.
Molloy et al., J. Organomet. Chem. 1989, 365, 61-73.
Bookser, Tetrahedron Lett. 2000, 41, 2805-2809.
Nicolaou et al., Chem. Eur. J. 2000, 6, 2783-2800.
Giannakakou et al., J. Biol. Chem. 1997, 272, 17118-17125.
Giannakakou et al., Proc. Natl. Acad. Sci. USA 2000, 97, 2904-2909.
Altmann et al., Bioorg. Med. Chem. Lett. 2000, 10, 2765-2768.
Skehan et al., J. Natl. Cancer Inst. 1990, 82, 1107-1112.

* cited by examiner

Primary Examiner — Nizal Chandrakumar
(74) Attorney, Agent, or Firm — Husch Blackwell LLP

(57) ABSTRACT

A highly active synthetic epothilone compound whose activity exceeds that of either epothilone EpoA or EpoB when assayed as a cytotoxic agent against a cancer cell line is disclosed as is a pharmaceutical composition containing the synthetic epothilone.

24 Claims, No Drawings

CHEMICAL SYNTHESIS OF A HIGHLY POTENT EPOTHILONE

GOVERNMENTAL SUPPORT

The present invention was made with governmental support pursuant to USPHS grant CA088822 from the National Institutes of Health. The government has certain rights in the invention.

TECHNICAL FIELD

The present invention relates to a synthetic analogue of a natural product called an epothilone. More particularly, the invention contemplates highly active epothilone compounds whose activity exceeds that of either epothilone EpoA or EpoB when assayed as a cytotoxic agent against a cancer cell line.

BACKGROUND ART

Ever since the official debut of the epothilones in 1996 [e.g. EpoA (Compound 1) and EpoB (Compound 2), [Höfle et al., Angew. Chem. 1996, 108, 1671-1673; Angew. Chem. Int. Ed. 1996, 35, 1567-1569.] synthetic chemists have been enamored with their structures,

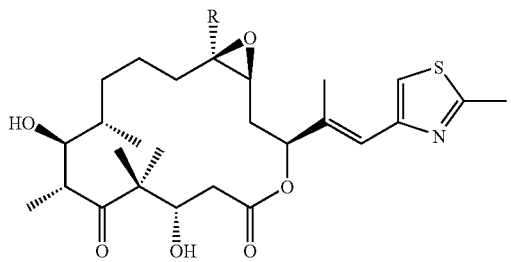

1: R = H (Epothilone A, EpoA)
2: R = Me (Epothilone B, EpoB)

both from the synthesis and modification points of view. [a) Altmann, Org. Biomol. Chem. 2004, 2, 2137-2152; b) Watkins et al., Curr. Pharm. Design 2005, 11, 1615-1653; c) Nicolaou et al., Chem. Commun. 2001, 1523-1535; d) Nicolaou et al., Pure Appl. Chem. 1999, 71, 989-997; e) Harris et al., J. Org. Chem. 1999, 64, 8434-8456; f) Nicolaou et al., Angew. Chem. 1998, 110, 2120-2153; Angew. Chem. Int. Ed. 1998, 37, 2014-2045] This rather intense and persistent interest is neither surprising nor without merit, for these naturally occurring substances have proven themselves challenging targets for synthesis, powerful tools in biology, and worthy-drug candidates currently in clinical trials [a) Okuno et al., J. Clin. Oncol. 2005, 23, 3069-3073; b) Altmann, Curr. Pharm. Design 2005, 11, 1595-1613; c) Rivkin et al., Angew. Chem. 2005, 117, 2898-2910; Angew. Chem. Int. Ed. 2005, 44, 2838-2850; d) Kolman, Curr. Opin. Invest. Drugs 2004, 5, 1292-1297; e) Kolman, Curr. Opin. Invest. Drugs 2004, 5, 657-667; f) Galmarini et al., iDrugs 2003, 6, 1182-1187; g) Biswas et al., J. Am. Chem. Soc. 2002, 124, 9825-9832] as anticancer agents.

Structure activity relationship (SAR) studies within the epothilone class of the present inventors and co-workers [Nicolaou et al., Chem. Commun. 2001, 1523-1535; Nicolaou et al., Pure Appl. Chem. 1999, 71, 989-997; Nicolaou et al., Angew. Chem. 1998, 110, 2120-2153; Angew. Chem. Int. Ed. 1998, 37, 2014-2045; a) Buey et al., Chem. Biol. 2004, 11, 225-236; Nicolaou et al., Angew. Chem. 2003, 115, 3639-3644; Angew. Chem., Int. Ed. 2003, 42, 3515-3520; Nicolaou et al., Tetrahedron 2002, 58, 6413-6432; Nicolaou et al., J. Am. Chem. Soc. 2001, 123, 9313-9323; Nicolaou et al., Chem. Biol. 2000, 7, 593-599] defined a narrow range of structural motifs that, when present, endow the epothilone molecule with biological activity and resulted in several potent epothilones such as the methylthio EpoB analogue Compound 3 [Nicolaou et al., Tetrahedron 2002, 58, 6413-6432] and Compound 4 [Nicolaou et al.,

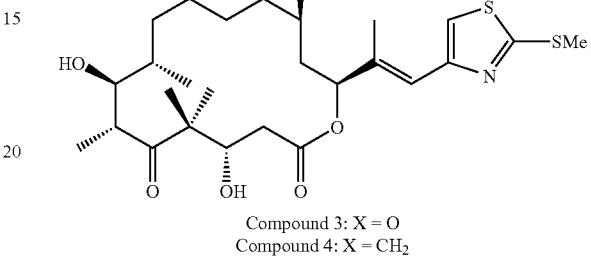

Compound 3: X = O
Compound 4: X = CH$_2$

Angew. Chem. 2003, 115, 3639-3644; Angew. Chem., Int. Ed. 2003, 42, 3515-3520]. This model was more or less confirmed by a recent electron crystallographic and nuclear-magnetic resonance-based conformational analysis [Nettles et al., Science 2004, 305, 866-869; Heinz et al., Angew. Chem. 2005, 117, 1324-1327; Angew. Chem. Int. Ed. 2005, 44, 1298-1301] of a tubulin-EpoA complex that appears to accommodate most of the published SAR data.

As discussed further below, a new study based on the above model led to the identification of the most potent, natural or designed, epothilone compounds reported to date.

BRIEF SUMMARY OF THE INVENTION

The present invention contemplates an epothilone compound. One contemplated compound corresponds in structure to Formula A-1, A-2, A-3 or A-4, below

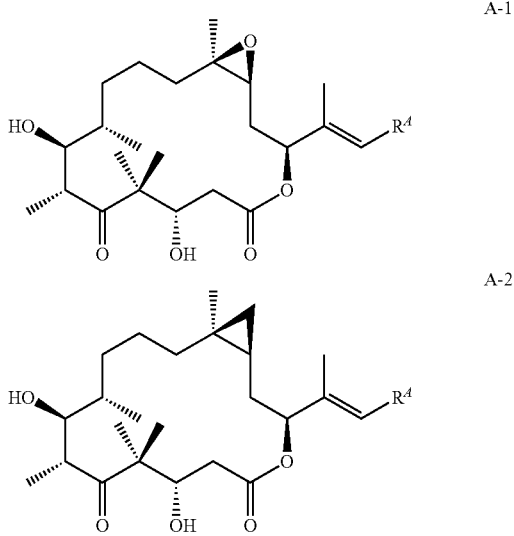

-continued

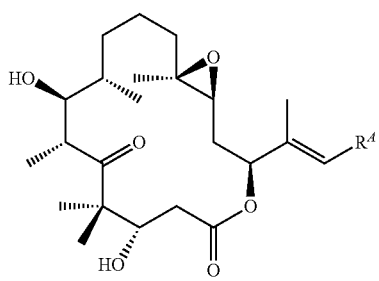
A-3

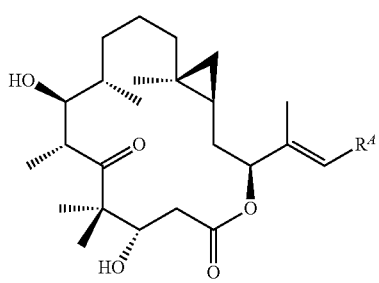
A-4 wherein $R^A$ is an aromatic ring having the structure

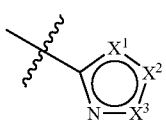

where each of $X^1$, $X^2$ and $X^3$ is independently S, $NR^1$, N, CH, or $CR^2$, such that the depicted five-membered ring contains at least two ring atoms that are other than carbon, or $X^2$ and $X^3$ together form a six-membered aromatic ring fused to the depicted five-membered ring that contains at least two ring atoms that are other than carbon, $R^1$ is selected from the group consisting of $C_1$-$C_8$-hydrocarbyl and methylene-$C_1$-$C_8$-hydrocarbylether, and $R^2$ is selected from the group consisting of $C_1$-$C_8$-hydrocarbyl, O—$C_1$-$C_8$-hydrocarbyl, halo, S—$C_1$-$C_8$-hydrocarbyl, methylenethio-$C_1$-$C_8$-hydrocarbyl and methylenethio-$C_1$-$C_8$-acyl.

Another contemplated compound corresponds in structure to Formula B-1, B-2, B-3 or B-4

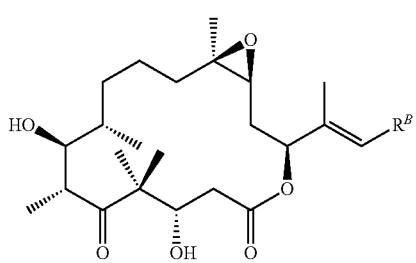
B-1

-continued

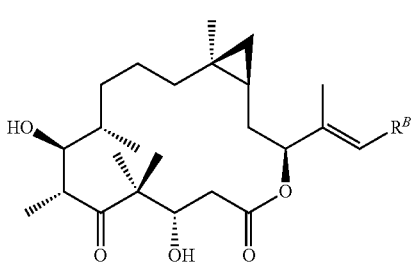
B-2

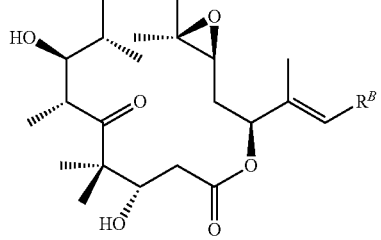
B-3

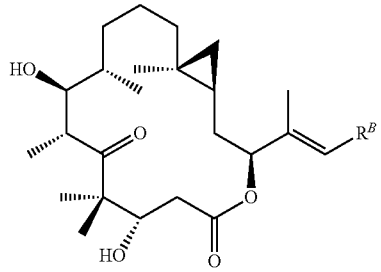
B-4 wherein $R^B$ is an aromatic ring having the structure

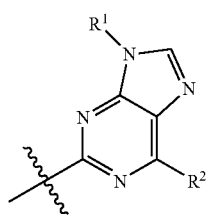

where $R^1$ is selected from the group consisting of $C_1$-$C_8$-hydrocarbyl and methylene-$C_1$-$C_8$-hydrocarbylether, and $R^2$ is selected from the group consisting of $C_1$-$C_8$-hydrocarbyl, O—$C_1$-$C_8$-hydrocarbyl, halo, S—$C_1$-$C_8$-hydrocarbyl, methylenethio-$C_1$-$C_8$-hydrocarbyl and methylenethio-$C_1$-$C_8$-acyl.

The contemplated epothilone compounds are pharmaceutically active and a composition containing a pharmaceutically effective amount of a compound of Formula A-1/A-4 or Formula B-1/B-4 dissolved or dispersed in a pharmaceutically acceptable diluent is also contemplated.

DETAILED DESCRIPTION OF THE INVENTION

The present invention contemplates epothilone compounds in which the 2-methyl-4-thiazyl substituent is replaced by another nitrogen-containing aromatic ring substituent. In one embodiment, a contemplated epothilone compound corresponds in structure to, Formula A-1, A-2, A-3 or A-4, below A-1
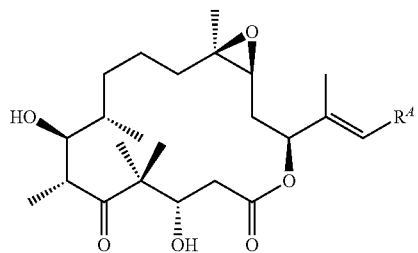

A-2
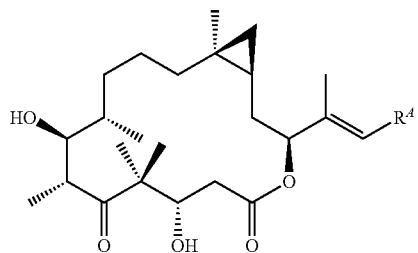

A-3
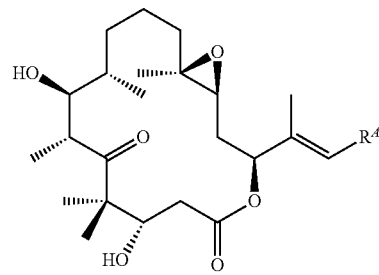

A-4
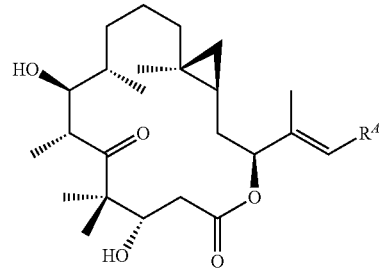

wherein $R^A$ is ring substituent having the structure

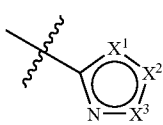

wherein the depicted five-membered ring is aromatic and contains at least two ring atoms that are other than carbon,
each of $X^1$, $X^2$ and $X^3$ is independently S, $NR^1$, N, CH, or $CR^2$,
$R^1$ is $C_1$-$C_8$-hydrocarbyl or methylene-$C_1$-$C_8$-hydrocarbylether, and
$R^2$ is selected from the group consisting of $C_1$-$C_8$-hydrocarbyl, O—$C_1$-$C_8$-hydrocarbyl, halo, S—$C_1$-$C_8$-hydrocarbyl, methylenethio-$C_1$-$C_8$-hydrocarbyl and methylenethio-$C_1$-$C_8$-acyl, with the proviso that when $X^2$ is S and $X^3$ is $CR^2$, $R^2$ is other than $C_1$-$C_8$-hydrocarbyl or S—$C_1$-$C_8$-hydrocarbyl, or
$X^2$ and $X^3$ together form a six-membered aromatic ring fused to the depicted five-membered aromatic ring.

Particularly preferred $R^A$ substituents are shown below

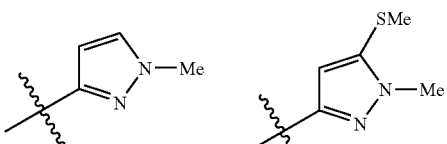

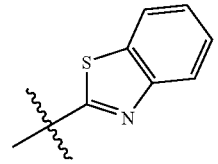

Another contemplated compound corresponds in structure to Formula B-1, B-2, B-3 or B-1
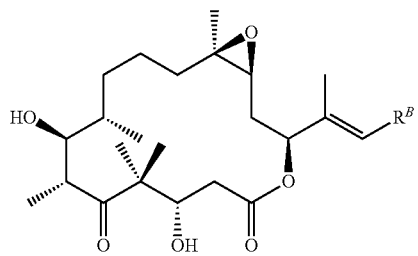

B-2
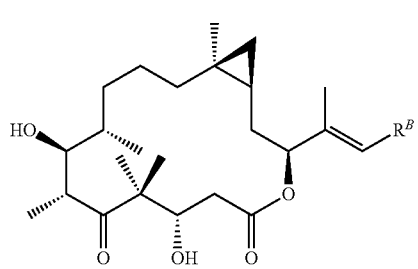

B-3
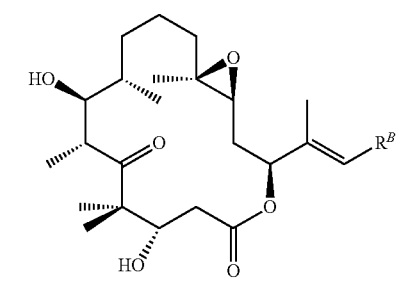

B-4
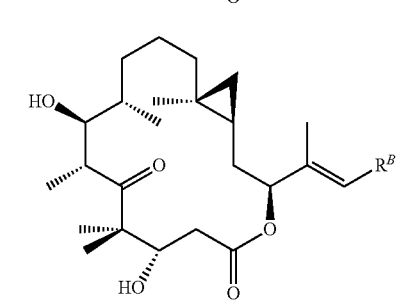

wherein $R^B$ is an aromatic ring having the structure

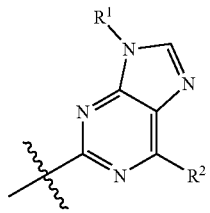

where $R^1$ is selected from the group consisting of $C_1$-$C_8$-hydrocarbyl and methylene-$C_1$-$C_8$-hydrocarbylether, and $R^2$ is selected from the group consisting of $C_1$-$C_8$-hydrocarbyl, O—$C_1$-$C_8$-hydrocarbyl, halo, S—$C_1$-$C_8$-hydrocarbyl, methylenethio-$C_1$-$C_8$-hydrocarbyl and methylenethio-$C_1$-$C_8$-acyl.

Particularly preferred $R^B$ substituents include

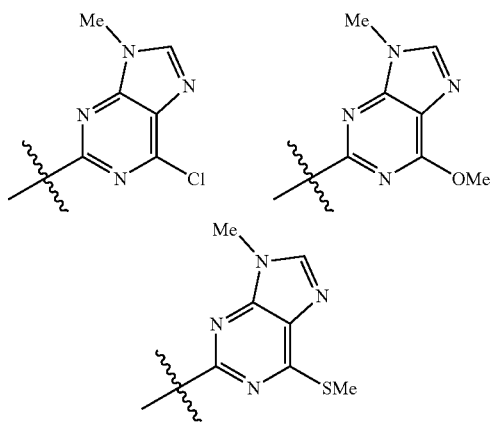

Preferred compounds can thus be grouped together as corresponding in structure to Formula C-1, C-2, C-3 or C-4

C-1

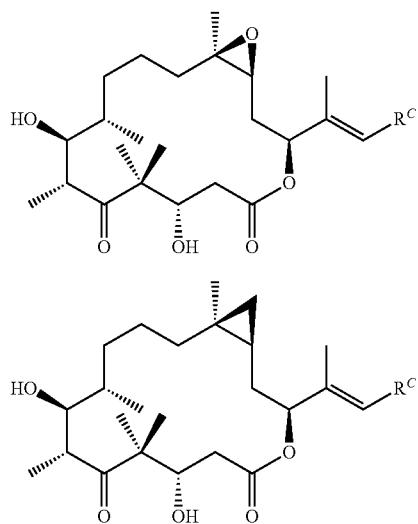

C-2

-continued

C-3

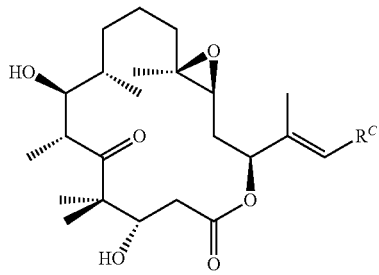

C-4

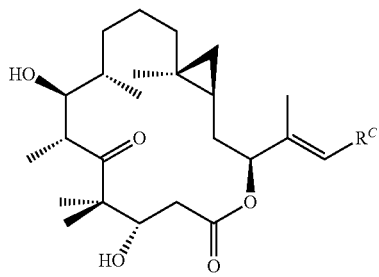

wherein $R^C$ is selected from the group consisting of

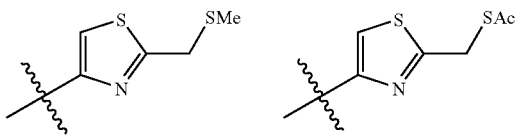
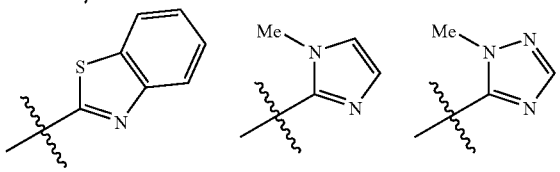
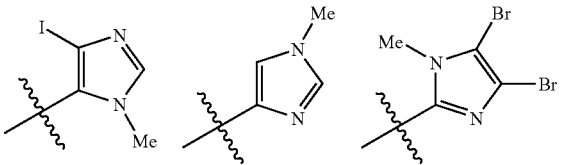
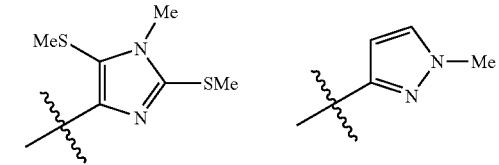
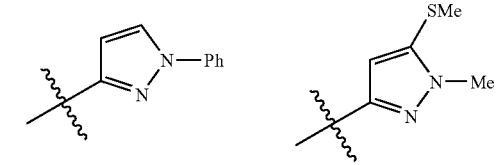
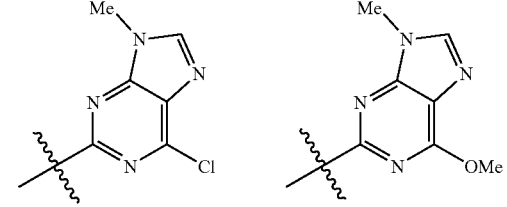

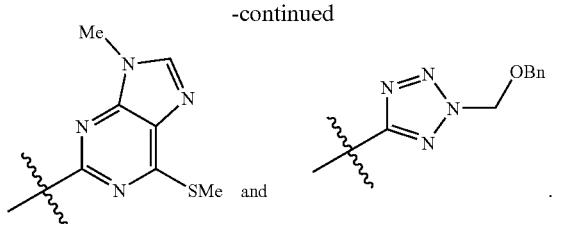

The cyano epothilone Compound 21 was not found active in these assays, but is a useful intermediate compound in the preparation of tetrazole epothilones such as Compound 20.

The word "hydrocarbyl" is used herein as a short hand term to include aliphatic as well as alicyclic groups or radicals that contain only carbon and hydrogen. Thus, alkyl, alkenyl and alkynyl groups are contemplated as are aralkyl groups such as benzyl and phenethyl, and aromatic hydrocarbons such as phenyl and naphthyl groups are also included. Where a specific hydrocarbyl substituent group is intended, that group is recited; i.e., $C_1$-$C_4$ alkyl, methyl or dodecenyl. Exemplary hydrocarbyl groups contain a chain of 1 to 12 carbon atoms, and preferably one to about 6 carbon atoms. Methyl is a particularly preferred hydrocarbyl group. It is noted that a skilled worker would understand that an alkenyl or alkynyl substituent must have at least two carbon atoms.

A $C_1$-$C_8$-hydrocarbyloxy or O—$C_1$-$C_8$-hydrocarbyl group is an ether containing a hydrocarbyl group linked to an oxygen atom. Similarly, a $C_1$-$C_8$-hydrocarbylthio or S—$C_1$-$C_8$-hydrocarbyl group is a thio ether. A methylene-$C_1$-$C_8$-hydrocarbylether contains a methylene group (—$CH_2$—) bonded to a depicted aromatic ring and to a hydrocarbylether (—$CH_2$—O—$C_1$-$C_8$-hydrocarbyl). Similarly, a methylenethio-$C_1$-$C_8$-hydrocarbyl group contains a methylene group bonded to the depicted ring and a thio ether hydrocarbyl group (—$CH_2$—S—$C_1$-$C_8$-hydrocarbyl). A methylenethio-$C_1$-$C_8$-acyl group contains a methylene group bonded to the depicted ring and a thio acyl hydrocarbyl group [—$CH_2$—S—(CO)$C_1$-$C_7$-hydrocarbyl]. A halo group is a halide substituent selected from the group consisting of fluoride, chloride, bromide and iodide.

From the several regions of the epothilone structure where modification could be made with potential to improve the activity of the molecule, the heterocyclic-containing side-chain domain was chosen. Having previously established the importance of the basic nitrogen in its specific location, [Nicolaou et al., Chem. Biol. 2000, 7, 593-599] that condition was set as a structural requirement for any new designs and the remainder of the structure of EpoB was maintained intact. These limits had the advantage that any potential drug (Compound I) candidate that could emerge from the investigation could, in principle, be produced either by total synthesis or through semisynthesis from a degradation-derived advanced intermediate (Compound II) and a heterocyclic stannane (Compound III) by, for example, a palladium-catalyzed cross-coupling reaction such as the Stille reaction [Nicolaou et al., Tetrahedron 2002, 58, 6413-6432] as indicated retrosynthetically below.

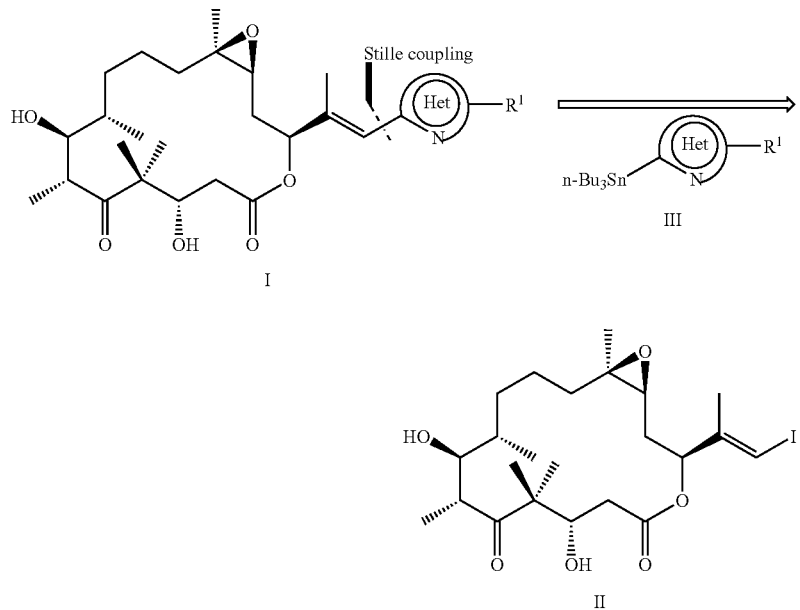

Epothilone Compounds 5-21 (below) are within the series of compounds corresponding in structure to Formula A-1 and were designed within the structural domains mentioned above and with certain additional rationales. The beneficial effect of certain lipophilic substituents, such as methyl and methylthio groups, on tubulin binding and cytotoxicity did not escape our attention, and thus the introduction of such moieties on several of these designs (Compounds 5-20). We also wanted to probe the effect of additional rings on the heterocyclic side-chain (Compounds 7, 17-19, 20) as well as the absence of a ring on that chain (Compound 21). Finally, we wished to challenge the ability of the tubulin receptor pocket to accommodate bulky halogen substituents (Compounds 10, 12).

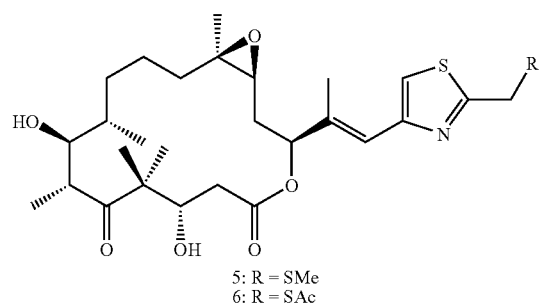
5: R = SMe
6: R = SAc
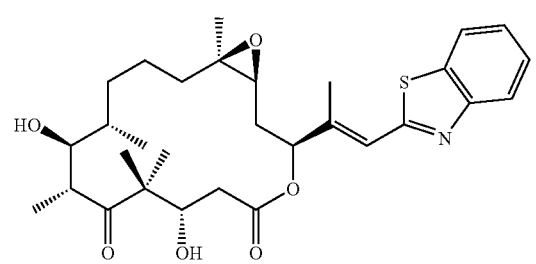
7
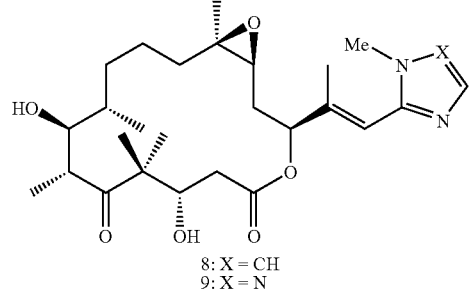
8: X = CH
9: X = N
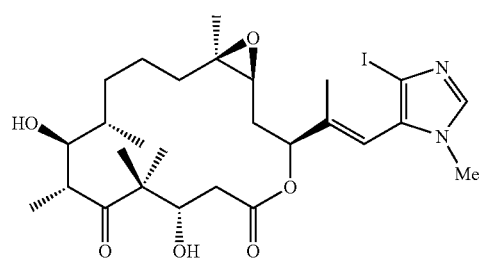
10
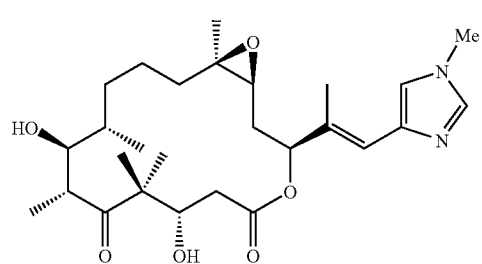
11
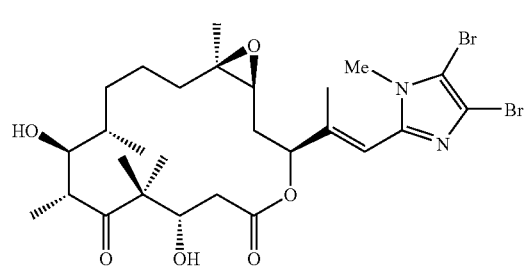
12
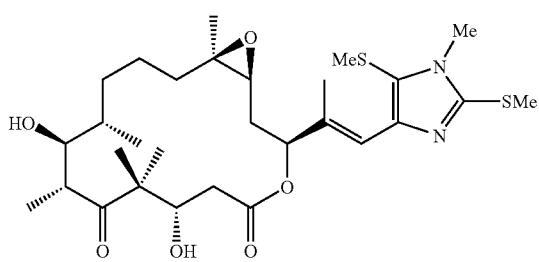
13
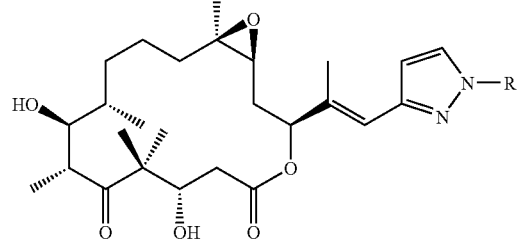
14: R = Me
15: R = Ph
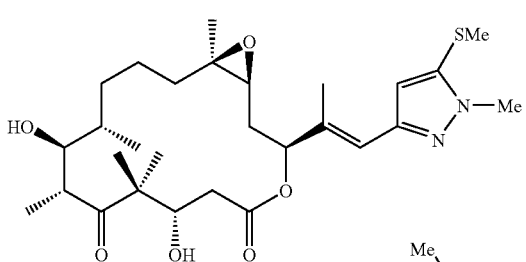
16
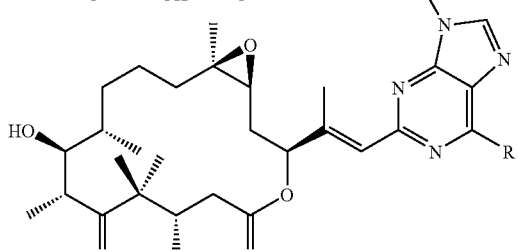
17: R = Cl
18: R = OMe
19: R = SMe
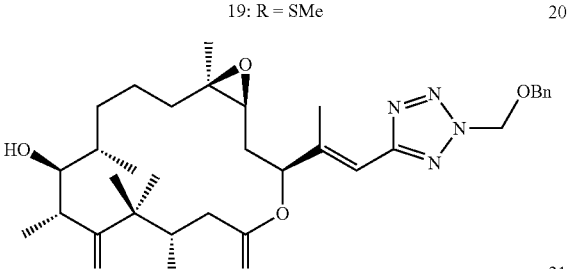
20
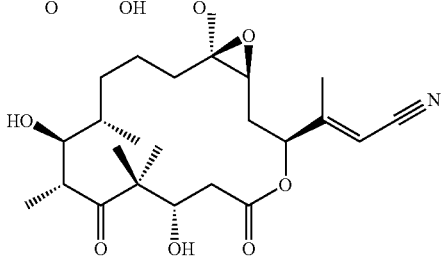
21

Syntheses of compounds corresponding to the analogous cyclopropane analogue and trans-fused analogues of each of the cis-oxirane (above) and cyclopropane compounds are illustrated hereinbelow in Schemes A and B, hereinbelow, wherein $R^C$ is defined elsewhere.
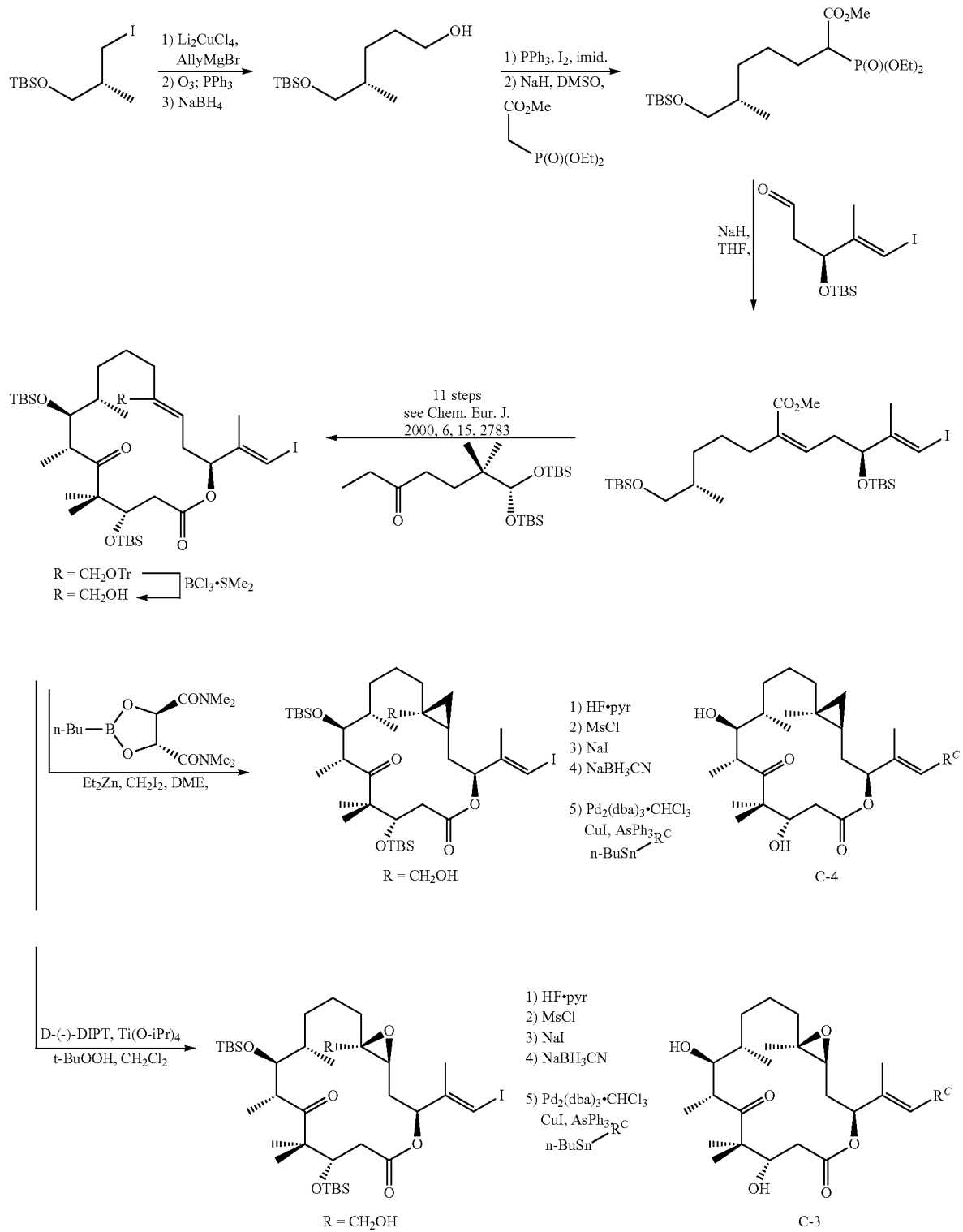
Scheme A

Scheme B (continued)

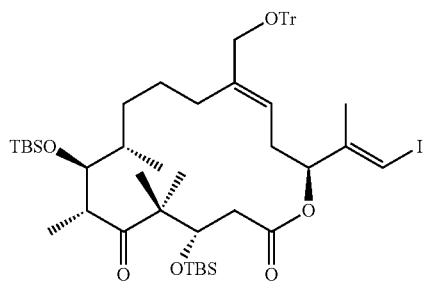 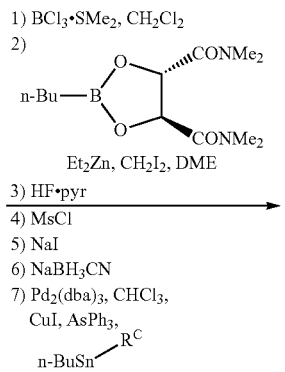 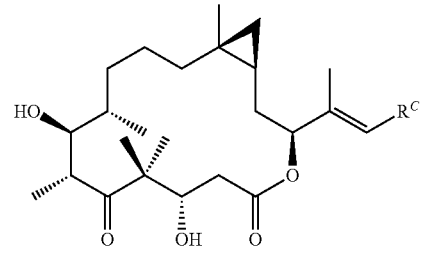

1) BCl$_3$·SMe$_2$, CH$_2$Cl$_2$
2) n-Bu—B with dioxaborolane bearing CONMe$_2$ groups, Et$_2$Zn, CH$_2$I$_2$, DME
3) HF·pyr
4) MsCl
5) NaI
6) NaBH$_3$CN
7) Pd$_2$(dba)$_3$, CHCl$_3$, CuI, AsPh$_3$, n-BuSn-R$^C$

C-2

Pharmaceutical Composition

An epothilone compound useful in the present invention can be formulated as a pharmaceutical composition. Such a composition contains an effective amount of the epothilone dissolved or dispersed in a pharmaceutically acceptable carrier or diluent. A contemplated composition can then be administered orally, parenterally, by inhalation spray, rectally, or topically in dosage unit formulations containing conventional nontoxic pharmaceutically acceptable carriers, adjuvants, and vehicles as desired. Topical administration can also involve the use of transdermal administration such as transdermal patches or iontophoresis devices. The term parenteral as used herein includes subcutaneous injections, intravenous, intramuscular, intrasternal injection, or infusion techniques. Formulation of drugs is discussed in, for example, Hoover, John E., *Remington's Pharmaceutical Sciences*, Mack Publishing Co., Easton, Pa.; 1975 and Liberman, H. A. and Lachman, L., Eds., *Pharmaceutical Dosage Forms*, Marcel Decker, New York, N.Y., 1980.

Injectable preparations, for example, sterile injectable aqueous or oleaginous suspensions can be formulated according to the known art using suitable dispersing or wetting agents and suspending agents. The sterile injectable preparation can also be a sterile injectable solution or suspension in a nontoxic parenterally acceptable diluent or solvent, for example, as a solution in 1,3-butanediol. Among the acceptable vehicles and solvents that can be employed are water, Ringer's solution, and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid find use in the preparation of injectables. Dimethyl acetamide, surfactants including ionic and non-ionic detergents, polyethylene glycols can be used. Mixtures of solvents and wetting agents such as those discussed above are also useful.

Suppositories for rectal administration of the drug can be prepared by mixing the drug with a suitable nonirritating excipient such as cocoa butter, synthetic mono- di- or triglycerides, fatty acids and polyethylene glycols that are sold at ordinary temperatures but liquid at the rectal temperature and will therefore melt in the rectum and release the drug.

Solid dosage forms for oral administration can include capsules, tablets, pills, powders, and granules. In such solid dosage forms, the compounds of this invention are ordinarily combined with one or more adjuvants appropriate to the indicated route of administration. If administered per os, the compounds can be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets can contain a controlled-release formulation as can be provided in a dispersion of active compound in hydroxypropylmethyl cellulose. In the case of capsules, tablets, and pills, the dosage forms can also comprise buffering agents such as sodium citrate, magnesium or calcium carbonate or bicarbonate. Tablets and pills can additionally be prepared with enteric coatings.

The epothilone can be delivered as a conjugate to antibodies or other agents that render them more selective. Epothilone nanoparticles in which the agent is encapsulated or covalently bound can also be employed for their administration, as such means can increase the efficacy and selectivity of the epothilone utilized.

For therapeutic purposes, formulations for parenteral administration can be in the form of aqueous or non-aqueous isotonic sterile injection solutions or suspensions. These solutions and suspensions can be prepared from sterile powders or granules having one or more of the carriers or diluents mentioned for use in the formulations for oral administration. The compounds can be dissolved in water, polyethylene glycol, propylene glycol, ethanol, corn oil, cottonseed oil, peanut oil, sesame oil, benzyl alcohol, sodium chloride, and/or various buffers. Other adjuvants and modes of administration are well and widely known in the pharmaceutical art.

Liquid dosage forms for oral administration can include pharmaceutically acceptable emulsions, solutions, suspensions, syrups, and elixirs containing inert diluents commonly used in the art, such as water. Such compositions can also comprise adjuvants, such as wetting agents, emulsifying and suspending agents, and sweetening, flavoring, and perfuming agents.

The amount of active ingredient that can be combined with the carrier materials to produce a single dosage form varies depending upon the mammalian host treated and the particular mode of administration.

Specific Compound Synthesis

For the synthesis of the specific epothilones and according to the previously noted retrosynthetic analysis, the corresponding heterocyclic stannanes were needed. These compounds were prepared either as shown in Scheme 1 (Compounds 26a-b, 28, 30a-b, 32, 33, 35a-c, 37a-b).

Scheme 1

Synthesis of stannane coupling partners
Reagents and conditions:

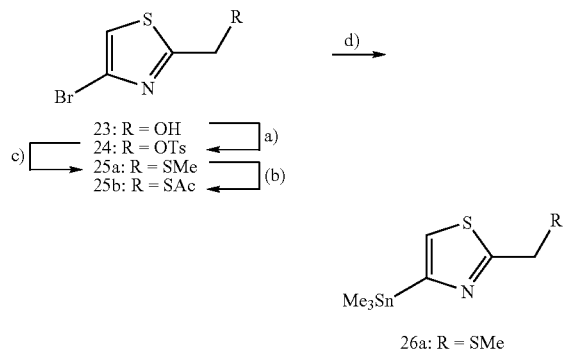

a) TsCl (1.5 equiv), Et$_3$N (3.0 equiv), 4-DMAP (0.1 equiv), CH$_2$Cl$_2$, 25° C., 1 hour, 84%; b) thioacetic acid (1.1 equiv), Et$_3$N (1.1 equiv), CH$_2$Cl$_2$, 0→25° C., 1 hour, 78%; c) NaSMe (3.0 equiv), EtOH, 25° C., 10 minutes, 97%; d) (Me$_3$Sn)$_2$ (7.0 equiv), [Pd(PPh$_3$)$_4$] (0.1 equiv), toluene, 110° C., 1 hour, 25a (26a, 95%), 25b (26b, 63%).

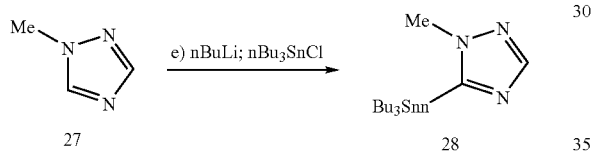

e) nBuLi (1.0 equiv), methylcyclohexane, THF, −78° C., 10 hours; then nBu$_3$SnCl (1.0 equiv), −78° C., 1 hour, 83%.

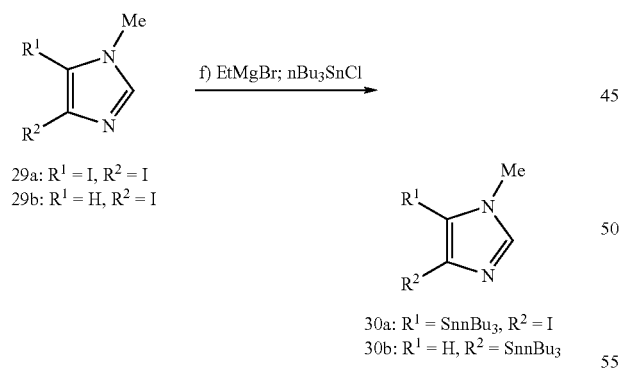

f) EtMgBr (1.0 equiv), THF, 25° C., 1.5 hours; then nBu$_3$SnCl (1.1 equiv), 25° C., 1 hour, 29a (30a, 74%), 29b (30b, 79%).

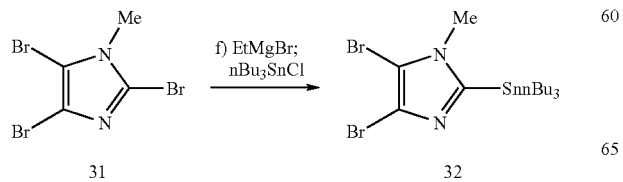

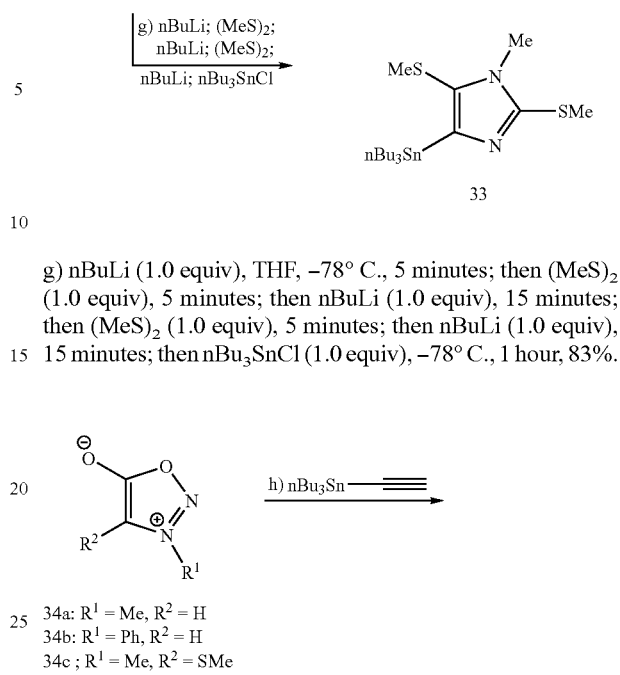

g) nBuLi (1.0 equiv), THF, −78° C., 5 minutes; then (MeS)$_2$ (1.0 equiv), 5 minutes; then nBuLi (1.0 equiv), 15 minutes; then (MeS)$_2$ (1.0 equiv), 5 minutes; then nBuLi (1.0 equiv), 15 minutes; then nBu$_3$SnCl (1.0 equiv), −78° C., 1 hour, 83%.

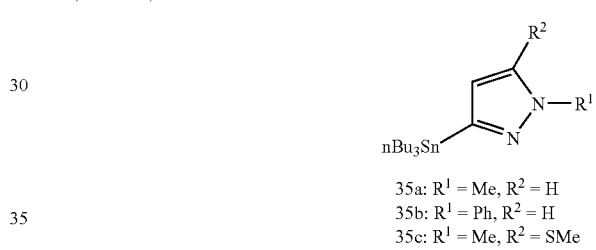

h) nBu$_3$SnCCH (1.5 equiv), xylenes, 138° C., 6 hours, 34a (35a, 41%), 34b (35b, 76%), 34c (35c, 30%).

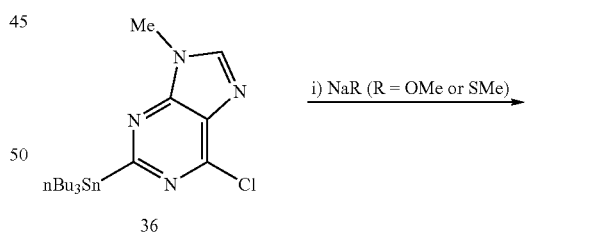

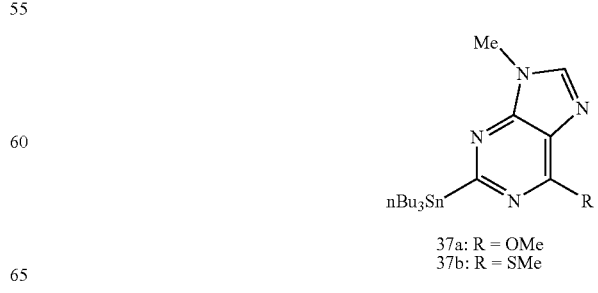

i) NaOMe or NaSMe (3.0 equiv), tBuOK (2.0 equiv), iPrOH, 25° C., 15 minutes, (37a, 10%) (37b, 89%).
Ts=p-Toluenesulfonyl; Et₃N=triethylamine; DMAP=4-Dimethylaminopyridine; Bn benzyl; THF=tetrahydrofuran.

Other compounds were prepared by known literature procedures {Compounds 35b [Sakamoto et al., *Heterocycles* 1992, 33, 813-818]; 36 [Kato et al., *J. Org. Chem.* 1997, 62, 6833-684]; 38-39 [Molloy et al., *J. Organomet. Chem.* 1989, 365, 61-73]; 40 [Bookser, *Tetrahedron Lett.* 2000, 41, 2805-2809]; and 41 [commercially available]}.

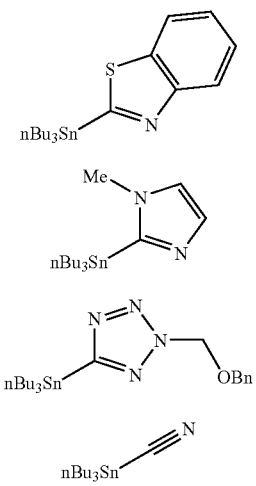

The attachment of each heterocyclic moiety onto the epothilone scaffold was then accomplished by Stille coupling [Nicolaou et al., *Tetrahedron* 2002, 58, 6413-6432] of each stannane with vinyl iodide Compound 22 [Nicolaou et al., *Chem. Eur. J.* 2000, 6, 2783-2800] to afford the targeted epothilone Compounds 5-21 as shown in Scheme 2, below.

Scheme 2
Synthesis of epothilones 5-21
Reagents and conditions:

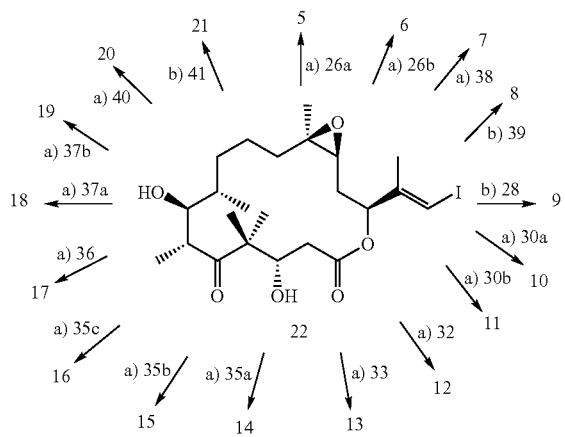

a) [Pd₂(dba)₃·CHCl₃] (0.2 equiv.), CuI (2.0 equiv.), AsPh₃ (0.8 equiv.), 26a (5, 74%), 26b (6, 40%), 38 (7, 55%), 30a (10, 43%), 30b (11, 68%), 32 (12, 76%), 33 (13, 79%), 35a (14, 71%), 35b (15, 66%), 35c (16, 60%), 36 (17, 52%), 37a (18, 39%), 37b (19, 53%), 40 (20, 56%), (2.0 equiv. of each stannane), DMF, 25° C., 3 hours.

b) [Pd(PPh₃)₄] (0.2 equiv.), CuI (2.0 equiv.), 39 (8, 51%), 28 (9, 47%), 41 (21, 34%) (2.0 equiv. of each stannane), DMF, 25° C., 3 hours. Yields are not optimized. dba=dibenzylidineacetone; DMF=N,N-Dimethylformamide.

The synthesized epothilones were tested in cytotoxicity assays for their growth inhibition properties and compared to either Taxotere™ or Taxol™ and either EpoA or EpoB. The results against several drug-sensitive and drug-resistant human cancer cell lines are summarized in Tables 1A-1C, below.

TABLE 1A

Cytotoxicity of designed epothilones 5-21[a]

| | Cell Line and IC$_{50}$ | | |
|---|---|---|---|
| | 1A9[b] | 1A9/PTX10[c] | |
| Compound | IC$_{50}$ | IC$_{50}$ | RR$_p$[d] |
| Taxol ™ | — | — | |
| Taxotere ™ | 1.5 ± 1.1 | 32.0 ± 6.8 | 21.3 |
| EpoA | 2.4 ± 2.6 | 5.1 ± 2.6 | 2.1 |
| EpoB | 0.99 ± 0.8 | 7.8 ± 4.6 | 7.9 |
| 5 | 3.6 ± 1.4 | 43.3 ± 12.0 | 12.0 |
| 6 | 5.4 ± 1.1 | 28.2 ± 9.3 | 5.2 |
| 7 | 0.19 ± 0.1 | 2.6 ± 2.5 | 13.7 |
| 8 | 95.5 ± 13.4 | >750 | — |
| 9 | 540 | >750 | — |
| 10 | >750 | >750 | — |
| 11 | 181 ± 81.6 | >750 | — |
| 12 | >750 | >750 | — |
| 13 | >750 | >750 | — |
| 14 | 0.50 ± 0.3 | 1.7 ± 1.1 | 3.4 |
| 15 | 5.45 ± 3.7 | 25.8 ± 19.8 | 4.7 |
| 16 | 0.06 ± 0.04 | 0.1 ± 0.0 | 1.7 |
| 17 | 3.7 ± 1.5 | 13.6 ± 7.3 | 3.7 |
| 18 | 3.7 ± 1.8 | 19.8 ± 10.6 | 5.4 |
| 19 | 1.0 ± 0.8 | 2.0 ± 1.5 | 2.0 |
| 20 | 4.0 ± 0.3 | 49.0 ± 7.0 | 12.3 |
| 21 | >750 | >750 | — |

[a]Compounds were tested for their antiproliferative effects in a 72 hour growth-inhibition assay using the methylene blue (KB-31 and KB-8511) or sulforhodamine-B (other cell lines) staining methods. [Nicolaou et al., Chem. Biol. 2000, 7, 593-599; Skehan et al., J. Natl. Cancer Inst. 1990, 82, 1107-1112] IC$_{50}$ values for each compound are given in nM and represent the mean of 3-5 independent experiments ± standard error of the mean.
[b]Human ovarian cancer cell line.
[c]Taxol ™-resistant 1A9 cell line expressing a single acquired point mutation at β270 (Phe→Val).
[d]Relative resistance of the parental cell line (RR$_p$) is calculated as the IC$_{50}$ value for each resistant cell line divided by that for the parental cell line.

TABLE 1B

Cytotoxicity of designed epothilones 5-21[a]

| | Cell Line and IC$_{50}$ 1A9/A8[e] | | Cell Line and IC$_{50}$ A2780/AD10[f] | |
|---|---|---|---|---|
| Compound | IC$_{50}$ | RR$_p$[d] | IC$_{50}$ | RR$_p$[d] |
| Taxol ™ | — | — | >150 | — |
| Taxotere ™ | 0.8 ± 0.2 | 0.5 | 29.4 ± 5.4 | 12.3 |
| EpoA | 41.0 ± 7.3 | 17.1 | 25.4 ± 8.6 | 25.7 |
| EpoB | 10.0 ± 1.4 | 10.1 | 56.5 ± 23.3 | 15.7 |
| 5 | 18.6 ± 11.3 | 5.2 | 82.2 ± 49.6 | 15.2 |
| 6 | 49.8 ± 34.5 | 9.2 | 8.6 ± 3.3 | 45.3 |
| 7 | 0.7 ± 0.4 | 3.7 | 707 | 7.4 |
| 8 | 242 | 2.5 | 760 | 1.4 |
| 9 | 627 | 1.2 | >750 | — |
| 10 | >750 | — | 1072 | 5.9 |
| 11 | 150 | 0.8 | >750 | — |
| 12 | >750 | — | 574 | — |
| 13 | 574 | — | 1.3 ± 0.3 | 2.6 |
| 14 | 0.8 ± 0.3 | 1.6 | 25.5 ± 15.1 | 4.7 |
| 15 | 4.8 ± 3.6 | 0.9 | 6.4 | 107 |
| 16 | 0.6 ± 0.5 | 10.0 | 30.3 ± 17.7 | 8.2 |
| 17 | 4.0 ± 2.5 | 1.1 | 46.3 ± 33.2 | 12.5 |
| 18 | 2.2 ± 1.6 | 0.6 | 47.3 ± 36.5 | 47.3 |

TABLE 1B-continued

Cytotoxicity of designed epothilones 5-21[a]

| Compound | Cell Line and IC$_{50}$ 1A9/A8[e] IC$_{50}$ | RR$_p$[d] | Cell Line and IC$_{50}$ A2780/AD10[f] IC$_{50}$ | RR$_p$[d] |
|---|---|---|---|---|
| 19 | 2.8 ± 2.2 | 2.8 | 67.0 ± 9.8 | 16.8 |
| 20 | 16.8 ± 9.2 | 4.2 | >750 | — |
| 21 | >750 | — | >150 | — |

See Table 1A for notes a and d.
[e]EpoA-resistant 1A9 cell line expressing a single acquired point mutation at β274 (Thr→Ile).
[f]Drug-resistant clone of the human ovarian carcinoma A2780 cell line overexpressing P-glycoprotein (Pgp) due to drug selection with adriamycin.

TABLE 1C

Cytotoxicity of designed epothilones 5-21[a]

| Compound | Cell Line and IC$_{50}$ KB-31[g] IC$_{50}$ | KB-8511[h] IC$_{50}$ | RRp[d] |
|---|---|---|---|
| Taxol ™ | 6.08 ± 1.19 | 1133 ± 74 | 186 |
| Taxotere ™ | — | — | — |
| EpoA | — | — | — |
| EpoB | 0.42 ± 0.03 | 0.39 ± 0.02 | 0.9 |
| 5 | 1.38 ± 0.05 | 1.97 ± 0.25 | 1.4 |
| 6 | 1.18 ± 0.12 | 8.39 ± 1.37 | 7.1 |
| 7 | 0.21 ± 0.07 | 0.08 ± 0.04 | 0.4 |
| 8 | 69.9 ± 5.31 | >1000 | — |
| 9 | 382 ± 49.4 | >1000 | — |
| 10 | >1000 | >1000 | — |
| 11 | 277 ± 122 | >1000 | — |
| 12 | >1000 | >1000 | — |
| 13 | 240 ± 34.0 | 247 ± 47.9 | 1.0 |
| 14 | 0.19 ± 0.01 | 0.25 ± 0.04 | 1.3 |
| 15 | 2.27 ± 0.16 | 1.62 ± 0.14 | 0.7 |
| 16 | 0.09 ± 0.01 | 0.14 ± 0.01 | 1.6 |
| 17 | 1.62 ± 0.22 | 20.2 ± 2.14 | 12.5 |
| 18 | 0.15 ± 0.09 | 7.45 ± 0.81 | 49.7 |
| 19 | 0.36 ± 0.17 | 6.21 ± 0.86 | 17.3 |
| 20 | 0.57 ± 0.08 | 4.44 ± 0.69 | 7.8 |
| 21 | 346 ± 10.5 | >1000 | — |

See Table 1A for notes a and d.
[g]Human epidermoid cancer cell line.
[h]Taxol ™-resistant (Pgp-overexpression) KB cell line.

The cell lines include the parental drug-sensitive ovarian carcinoma line 1A9, its Taxol™-resistant (1A9/PTX10) [Giannakakou et al., *J. Biol. Chem.* 1997, 272, 17118-17125] and EpoA-resistant (1A9/A8) [Giannakakou et al., *Proc. Natl. Acad. Sci. USA* 2000, 97, 2904-2909] sublines, as well as the mutant variant that overexpresses the Pgp-efflux pump (1A9/AD10). The Taxol™- and EpoA-resistant cell lines harboring distinct acquired β-tubulin mutations affect the drug-tubulin interaction and result in impaired taxane- and epothilone-driven tubulin polymerization. In addition, further cytotoxicity studies were carried out using a pair of drug-sensitive parental human epidermoid carcinoma cells (KB-31) and its Taxol™-resistant Pgp-overexpressing subline (KB-5811).

Compounds 5 and 6, although less potent than EpoB, exhibited high potency against several of the tested cell lines reflecting considerable tolerance of the receptor to the structural changes embodied within the molecules. The benzothiazole analogue Compound 7 exhibited excellent cytotoxicity across the range of cell lines, being more potent than EpoB. The significantly lower activities of the imidazole analogue Compounds 8 and 10-13 and the triazole epothilone Compound 9, point to difficulties of the N-methylimidazole moiety to fit into the tubulin receptor and translate into high potency, whereas the substitution pattern and crowded nature of Compound 13 underscores the requirement for the specific position of the basic nitrogen and planarity of the conjugated side-chain system.[13] [For a potent imidazole-containing epothilone B analogue, see Altmann et al., *Bioorg. Med. Chem. Lett.* 2000, 10, 12765-2768.]

Replacement of the thiazole ring with a pyrazole moiety resulted in excellent biological activity as evidenced by Compounds 14-16. The trio (14-16) provide interesting SARs. Thus, N—Me substituted pyrazole epothilone Compound 14 exhibited more potent cytotoxicities than EpoB across the board and its N-Ph counterpart (Compound 15) was somewhat less active, whereas the compound carrying the extra SMe substituent (Compound 16) proved to be the most potent of all compounds tested.

Indeed, the latter epothilone (Compound 16) exhibited a remarkable 17-fold activity increase against both the 1A9 parental and the 1A9/A8 EpoA-resistant cell lines and an even more impressive 78-fold increase in potency against the Taxol™-resistant 1A9/PTX10 cell line as compared to the naturally occurring EpoB. The action of Compound 16 against the KB cell lines is also impressive with a 3-5-fold potency increase as compared to EpoB. Interestingly, however, and despite its 4-fold potency enhancement over EpoB, Compound 16 was not as potent as Compound 14 (20-fold potency increase) as a growth inhibitor against the PgP-overexpressing cell line A2780/AD10.

The purine epothilone Compounds 17-19 showed comparable potencies across the entire range of cell lines tested to those of EpoB and, thus, represent a further expansion of the boundaries of steric bulk and electron cloud that can be tolerated by the tubulin receptor. Finally, the nitrile epothilone Compound 21 was found to be devoid of any significant cytotoxicity against any of the cell lines tested, confirming the importance of the basic heterocyclic moiety of the epothilone structure.

Relative activities of four selected highly potent epothilones (Compounds 3, 4, 7 and 16) against the previously discussed cell lines are shown below in Table 2.

TABLE 2

| Epothilone | Cell Line[a] | IC$_{50}$ | EpoB | RA$_{EpoB}$[b] |
|---|---|---|---|---|
| | 1A9 | 0.17 | 0.3 | 1.8 |
| | 1A9/PTX10 | 0.26 | 3.7 | 14.2 |
| | 1A9/A8 | 1.3 | 6.5 | 5.0 |
| | KB-31 | 0.11 | 0.19 | 1.7 |
| | KB-5811 | 0.07 | 0.18 | 2.6 |

3

TABLE 2-continued

| Epothilone | Cell Line[a] | IC$_{50}$ | EpoB | RA$_{EpoB}$[b] |
|---|---|---|---|---|
| 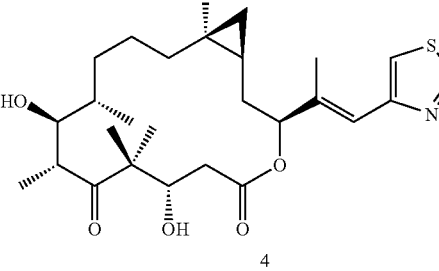 4 | 1A9<br>1A9/PTX10<br>1A9/A8<br>KB-31<br>KB-5811 | 0.1<br>0.7<br>2.4<br>0.20<br>0.12 | 0.6<br>3.1<br>6.5<br>0.19<br>0.12 | 6.0<br>4.4<br>2.7<br>1.0<br>1.0 |
| 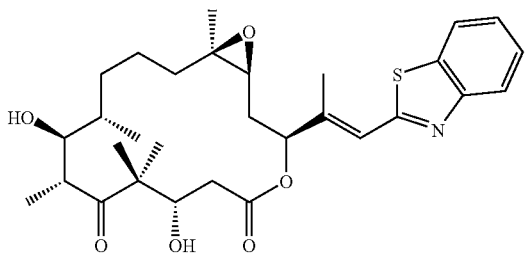 7 | 1A9<br>1A9/PTX10<br>1A9/A8<br>KB-31<br>KB-5811 | 0.19<br>2.6<br>0.7<br>0.21<br>0.08 | 0.99<br>7.8<br>10.0<br>0.42<br>0.39 | 5.2<br>3.0<br>14.3<br>2.0<br>4.9 |
| 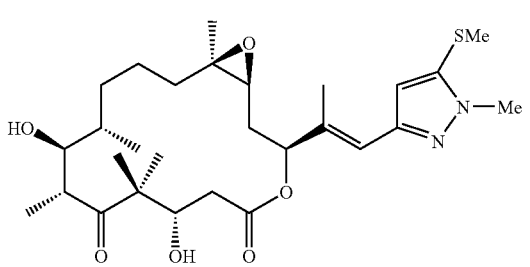 16 | 1A9<br>1A9/PTX10<br>1A9/A8<br>KB-31<br>KB-5811 | 0.06<br>0.1<br>0.6<br>0.09<br>0.14 | 0.99<br>7.8<br>10.0<br>0.42<br>0.39 | 16.5<br>78.0<br>16.7<br>4.7<br>2.8 |
| 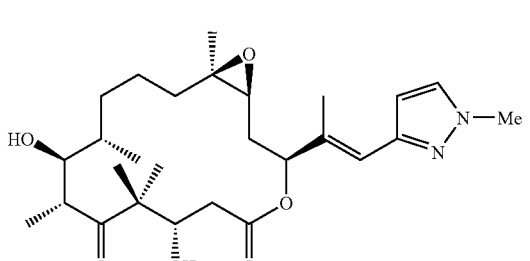 14 | 1A9<br>1A9/PTX10<br>1A9/A8<br>KB-31<br>KB-5811 | 0.5<br>1.7<br>0.8<br>0.19<br>0.25 | 0.99<br>7.8<br>10.0<br>0.42<br>0.39 | 2.0<br>4.6<br>12.5<br>2.2<br>1.6 |

[a]See Table 1A-1C for definitions of cell lines.
[b]Relative activity (RA EpoB) is defined as the ratio of the IC$_{50}$ value of EpoB to the IC$_{50}$ value of the tested compound in the concurrent biological assay. This value represents the fold-increase in potency of the tested compound compared to EpoB determined concurrently.

The striking biological profile of the pyrazole epothilone Compound 16 as compared to those of EpoB and potent analogue Compounds 3 [Nicolaou et al., *Tetrahedron* 2002, 58, 6413-6432], 4 [Nicolaou et al., *Angew. Chem.* 2003, 115, 3639-3644; *Angew. Chem., Int. Ed.* 2003, 42, 3515-3520], 7, and 14 (see Table 3), all synthesized in these laboratories, makes this analogue, to the best of our knowledge, the most potent epothilone known to date. Compound 16 outperformed EpoB in all five cancer cell lines tested, exhibiting particularly remarkable potency increases over the naturally occurring substance against the parental ovarian cell line 1A9 (16.5-fold), its Taxol™-resistant variant 1A9/PTX10 (78.0- fold) and its EpoA-resistant mutant 1A9/A8 (16.7-fold). Given that EpoB (Compound 2) and analogue Compound 3 have entered clinical trials {other notable clinical candidates from the epothilone class include those synthesized by Danishefsky [EpoD/KOS-862, Kolman et al., *Curr. Opin. Invest. Drugs* 2004, 5, 657-667; Epo-490, Kolman et al., *Curr. Opin. Invest. Drugs* 2004, 5, 657-667, and Fludelone, Rivkin et al., *Angew. Chem.* 2005, 117, 2898-2910; *Angew. Chem. Int. Ed.* 2005, 44, 2838-2850], Bristol-Myers Squibb [BMS 247550/ lactam EpoB, Okuno et al., *J. Clin. Oncol.* 2005, 23, 3069-3073 and BMS-310705/C-20 aminomethyl EpoB, Kolman, *Curr. Opin. Invest. Drugs* 2004, 5, 1292-1297] and Schering AG [ZK-EPO (Schering AG Press Release)} as anticancer agents, Compound 16 merits further investigation as a potential drug candidate.

Experimental Data for Compounds

A. General Procedures

All reactions were carried out under argon atmosphere with dry solvents under anhydrous conditions unless otherwise noted. Dry tetrahydrofuran (THF), toluene, benzene, diethyl ether ($Et_2O$), and methylene chloride ($CH_2Cl_2$) were obtained by passing commercially available pre-dried, oxygen-free formulations through activated alumina columns. Yields refer to chromatographically and spectroscopically ($^1H$ NMR) homogeneous materials unless otherwise stated. Reagents were purchased at the highest commercial quality and used without further purification, unless otherwise stated.

Reactions were monitored by thin-layer chromatography (TLC) carried out on 0.25 mm E. Merck silica gel plates (60F-254) using UV light as a visualizing agent and an ethanolic solution of p-anisaldehyde and phosphomolybdic acid, and heat as developing agents. E. Merck silica gel (60, particle size 0.040-0.063 mm) and Sigma-Aldrich Florisil® (~200 mesh) were used for flash column chromatography. Preparative thin-layer chromatography (PTLC) separations were carried out on 0.25 mm E. Merck silica gel plates (60F-254).

NMR spectra were recorded on Bruker DRX-600, DRX-500, AMX-500 or AMX-400 instruments and calibrated using residual undeuterated solvent as an internal reference. The following abbreviations were used to explain the multiplicities: s=singlet, d=doublet, t=triplet, q=quartet, m=multiplet, br=broad. IR spectra were recorded on a Perkin-Elmer 1600 series FT-IR spectrometer. Electrospray ionization (ESI) mass spectrometry (MS) experiments were performed on an API 100 Perkin-Elmer SCIEX single quadrupole mass spectrometer at 4000V emitter voltage. High-resolution mass spectra (HRMS) were recorded on a VG ZAB-ZSE mass spectrometer using MALDI (matrix-assisted laser-desorption ionization) or ESI (electrospray ionization). Optical rotations were recorded on a Perkin-Elmer 343 polarimeter.

B. General Procedure for Stille Coupling:

Method A:

To a solution of vinyl iodide Compound 22 (10.0 mg, 18.6 μmol, 1.0 equiv.), CuI (7.1 mg, 37.2 μmol, 2.0 equiv.), $AsPh_3$ (4.6 mg, 14.9 μmol, 0.8 equiv.) in degassed DMF (2 mL) was added $Pd_2(dba)_3 \cdot CHCl_3$ (3.9 mg, 3.7 μmol, 0.2 equiv.). The resulting solution was stirred for 5 minutes at 25° C. and then a solution of stannane (37.2 μmol, 2.0 equiv.) in degassed DMF (1 mL) was added drop-wise via syringe. The reaction mixture was stirred at room temperature for 3 hours, quenched with $H_2O$ (30 mL) and extracted with EtOAc (3×15 mL). The combined organic layers were washed with brine (15 mL), dried ($Na_2SO_4$) and concentrated in vacuo. Purification of the residue by flash column chromatography (silica gel) and PTLC afforded the desired epothilone analogue.

Method B:

To a solution of vinyl iodide Compound 22 (10.0 mg, 18.6 μmol, 1.0 equiv.) and CuI (7.1 mg, 37.2 μmol, 2.0 equiv.) in degassed DMF (2 mL) was added $Pd(PPh_3)_4$ (4.3 mg, 3.7 μmol, 0.2 equiv.). The resulting solution was stirred for 5 minutes at 25° C. and then a solution of stannane (37.2 μmol, 2.0 equiv.) in degassed DMF (1 mL) was added drop-wise via syringe. The reaction mixture was stirred at room temperature for 3 hours, quenched with $H_2O$ (30 mL) and extracted with EtOAc (3×15 mL). The combined organic layers were washed with $H_2O$ (20 mL), brine (15 mL), dried ($Na_2SO_4$) and concentrated in vacuo. Purification of the residue by flash column chromatography (silica gel) and subsequent PTLC afforded the desired epothilone analogue.

Epothilone Compound 5:

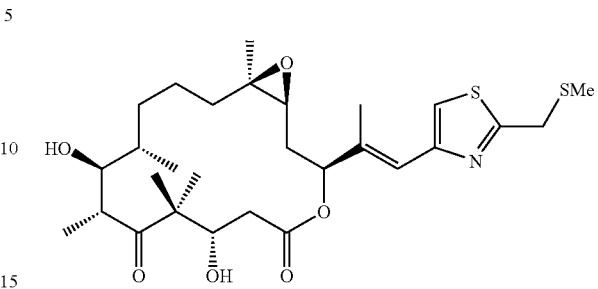

Method A; white foam; 74% yield; $R_f$=0.38 (silica gel, EtOAc:hexanes, 1:1); $[\alpha]_D^{32}$=−18.0 (MeOH, c=1.0); IR (film) $u_{max}$ 3443 br, 2964, 1732, 1714, 1694, 1682, 1454, 1384, 1250, 1051, 980, 914, 732 $cm^{-1}$; $^1H$ NMR (500 MHz, $CD_2Cl_2$) δ=7.13 (s, 1 H), 6.56 (s, 1 H), 5.39 (dd, J=2.7, 8.0 Hz, 1 H), 4.19 (d, J=9.7 Hz, 1 H), 3.96 (s, 2 H), 3.72 (s, 1 H), (br s, 1 H), 3.27 (dq, J=4.7, 6.8 Hz, 1 H), (dd, J=4.4, 8.0 Hz, 1 H), 2.50 (br s, 1 H), (dd, J=10.3, 14.2 Hz, 1 H), 2.36 (dd, J=3.2, Hz, 1 H), 2.16 (s, 3 H), 2.11 (s, 3 H), 2.10-2.05 (m, 1 H), 1.93 (td, J=8.2, 15.3 Hz, 1 H), 1.73-1.65 (m, 1 H), 1.55-1.36 (m, 6 H), 1.35 (s, 3 H), 1.26 (s, 3 H), 1.15 (d, J=6.9 Hz, 3 H), 1.05 (s, 3H), 0.99 ppm (d, J=7.0 Hz, 3 H); $^{13}C$ NMR (125 MHz, $CD_2Cl_2$) δ=219.9, 170.1, 168.1, 152.0, 137.5, 119.2, 117.2, 76.6, 73.8, 72.6, 61.4, 60.9, 52.7, 42.7, 39.0, 36.1, 35.0, 32.1, 31.9, 30.3, 22.1, 22.1, 21.1, 19.1, 16.6, 15.3, 15.0, 13.3 ppm; HRMS (ESI-TOF) calcd for $C_{28}H_{43}NO_6S_2^+$ $[M+H^+]$ 554.2604, found 554.2613.

Epothilone Compound 6:

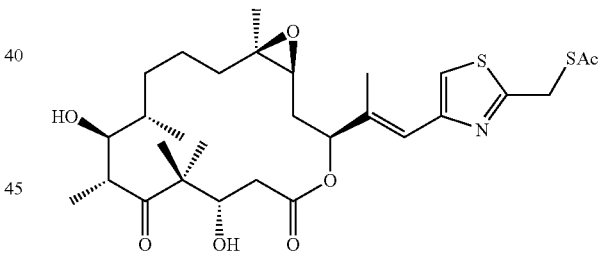

Method A; colorless oil; 40% yield; $R_f$=0.40 (silica gel, EtOAc:hexanes, 1:1); $[\alpha]_D^{32}$=−7.4 (DMSO, c=0.40); IR (film) $u_{max}$ 3423 br, 2958, 2928, 1736, 1691, 1466, 1380, 1251, 1135, 1096, 1054, 1008, 980, 957, 884, 711 $cm^{-1}$; $^1H$ NMR (500 MHz, $CD_2Cl_2$) δ=7.09 (s, 1 H), 6.54 (s, 1 H), 5.39 (dd, J=2.5, 8.1 Hz, 1 H), 4.40 (s, 2 H), 4.19 (m, 1 H), 3.72 (t, J=3.9 Hz, 1 H), 3.66-3.59 (m, 1 H), 3.27 (td, J=6.8, 11.5 Hz, 1 H), 2.79 (dd, J=4.4, 7.8 Hz, 1 H), 2.49 (dd, J=10.3, 14.3 Hz, 1 H), 2.40 (br s, 1 H), 2.39 (s, 3 H), 2.36 (dd, J=3.2, 14.2 Hz, 1 H), 2.09 (s, 3 H), 2.09-2.04 (m, 1 H), 1.92 (td, J=8.2, 15.2 Hz, 1 H), 1.73-1.65 (m, 1 H), 1.55-1.36 (m, 6 H), 1.35 (s, 3 H), 1.26 (s, 3 H), 1.15 (d, J=6.8 Hz, 3 H), 1.05 (s, 3 H), 0.99 ppm (d, J=7.0 Hz, 3H); $^{13}C$ NMR (125 MHz, $CD_2Cl_2$) δ=219.9, 193.5, 170.1, 165.5, 152.0, 137.7, 119.0, 117.3, 76.6, 73.9, 72.6, 61.3, 60.9, 52.7, 42.8, 39.0, 36.1, 32.0, 31.9, 30.3, 30.1, 29.8, 22.1, 22.1, 21.0, 19.1, 16.6, 15.0, 13.3 ppm; HRMS (ESI-TOF) calcd for $C_{29}H_{43}NO_7S_2^+$ $[M+H^+]$ 582.2554, found 582.2557.

Epothilone Compound 7:

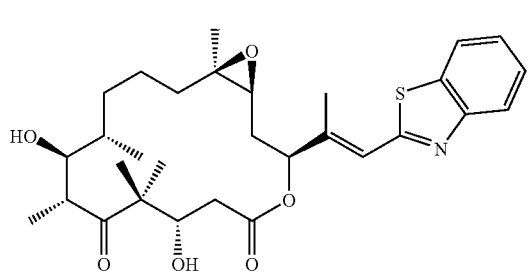

Method A; white foam; 550 yield; $R_f$=0.37 (silica gel, EtOAc:hexanes, 1:1); $[\alpha]_D^{32}$=−10 (DMSO, c=0.32); IR (film) $u_{max}$ 3441 br, 2959, 2919, 2356, 1738, 1725, 1714, 1682, 1650, 1454, 1379, 1248, 1143, 1056, 1002, 973, 882, 761, 730 cm$^{-1}$; $^1$H NMR (500 MHz, CDCl$_3$) δ=8.01 (d, J=8.2 Hz, 1 H), 7.89 (d, J=8.0 Hz, 1 H), 7.51-7.47 (m, 1 H), 7.41-7.37 (m, 1 H), 6.93 (s, 1 H), 5.54 (dd, J=3.7, 6.0 Hz, 1 H), 4.20 (d, J=9.3 Hz, 1 H), 3.97 (br s, 1 H), 3.80 (t, J=4.3 Hz, 1 H), 3.38-3.31 (m, 1 H), 2.83 (t, J=6.2 Hz, 1 H), 2.61 (dd, J=10.2, 14.0 Hz, 1 H), 2.50 (br s, 1 H), 2.46 (dd, J=3.5, 14.0 Hz, 1 H), 2.32 (s, 3H), 2.13-2.06 (m, 1 H), 2.05-1.98 (m, 1 H), 1.77-1.66 (m, 1 H), 1.59-1.32 (m, 6 H), 1.40 (s, 3 H), 1.29 (s, 3 H), 1.18 (d, J=6.8 Hz, 3 H), 1.09 (s, 3H), 1.01 ppm (d, J=6.9 Hz, 3 H); $^{13}$C NMR (150 MHz, CDCl$_3$) δ=220.7, 170.4, 164.6, 152.4, 144.8, 134.7, 126.5, 125.3, 122.8, 121.4, 119.4, 76.0, 74.5, 73.0, 61.3, 61.3, 53.0, 43.2, 38.9, 36.4, 31.7, 31.7, 30.5, 22.8, 21.2, 21.0, 20.1, 17.1, 17.0, 14.0 ppm; HRMS (ESI-TOF) calcd for C$_{30}$H$_{41}$NO$_6$S$^+$ [M+H$^+$]544.2727, found 544.2743.

Epothilone Compound 8:

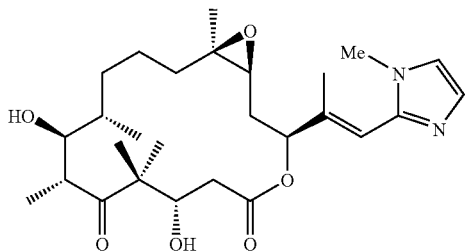

Method B; colorless film; 51% yield; $R_f$=0.32 (silica gel, EtOAc:acetone, 9:1); $[\alpha]_D^{32}$=−28 (DMSO, c=0.25); IR (film) $u_{max}$ 3438 br, 2968, 2927, 1732, 1714, 1693, 1682, 1470, 1451, 1383, 1283, 1250, 1146, 1054, 980, 739 cm$^{-1}$; $^1$H NMR (500 MHz, CD$_2$Cl$_2$) δ=7.02 (s, 1H), 6.87 (s, 1 H), 6.34 (s, 1 H), 5.51 (dd, J=3.0, 7.9 Hz, 1 H), 4.16 (dd, J=3.0, 10.4 Hz, 1 H), 3.70 (t, J=4.5 Hz, 1 H), 3.63 (br s, 1H), 3.61 (s, 3 H), 3.29-3.23 (m, 1 H), 2.80 (dd, J=4.6, 7.6 Hz, 1 H), 2.62 (br s, 1H), 2.47 (dd, J=10.4, 14.4 Hz, 1 H), 2.35 (dd, J=3.1, 14.4 Hz, 1H), 2.17 (s, 3 H), 2.10-1.96 (m, 2 H), 1.71-1.65 (m, 1 H), 1.56-1.34 (m, 6 H), 1.32 (s, 3 H), 1.26 (s, 3 H), 1.14 (d, J=6.8 Hz, 3 H), 1.03 (s, 3 H), 0.99 ppm (d, J=7.0 Hz, 3 H); $^{13}$C NMR (125 MHz, CD$_2$Cl$_2$) δ=219.8, 170.1, 144.0, 140.6, 127.4, 120.4, 112.6, 76.7, 73.9, 72.4, 61.2, 60.9, 54.6, 42.7, 39.1, 36.0, 32.5, 32.1, 31.6, 30.3, 22.1, 22.0, 21.1, 18.8, 16.6, 14.6, 13.2 ppm; HRMS (ESI-TOF) calcd for C$_{27}$H$_{42}$N$_2$O$_6^+$ [M+H$^+$] 491.3115, found 491.3120.

Epothilone Compound 9:

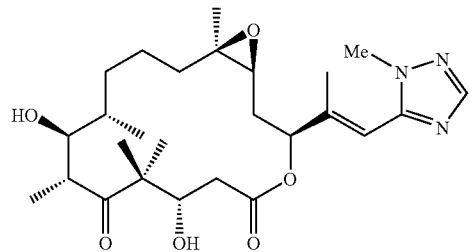

Method B; colorless film; 47% yield; $R_f$=0.35 (silica gel, EtOAc); $[\alpha]_D^{32}$=−23 (DMSO, c=0.043); IR (film) $u_{max}$ 3417 br, 2967, 2920, 1732, 1694, 1682, 1470, 1455, 1384, 1258, 1147, 1055, 1008, 979, 802, 656 cm$^{-1}$; $^1$H NMR (500 MHz, CD$_2$Cl$_2$) δ 7.81 (s, 1 H), 6.41 (s, 1 H), 5.49 (dd, J=3.0, 6.8 Hz, 1H), 4.15 (ddd, J=3.3, 7.1, 10.3 Hz, 1 H), 3.84 (s, 3 H), 3.72 (dd, J=4.0, 8.3 Hz, 1 H), 3.33-3.25 (m, 2 H), 2.79 (dd, J=5.8, 6.7 Hz, 1 H), 2.51 (dd, J=10.2, 14.6 Hz, 1 H), 2.43 (dd, J=3.4, 14.6 Hz, 1 H), 2.39 (br d, J=3.3 Hz, 1 H), 2.21 (s, 3 H), 2.10-1.97 (m, 2 H), 1.72-1.64 (m, 1 H), 1.56-1.35 (m, 6 H), 1.34 (s, 3 H), 1.27 (s, 3 H), 1.14 (d, J=6.9 Hz, 3 H), 1.04 (s, 3 H), 0.99 ppm (d, J=7.0 Hz, 3 H); $^{13}$C NMR (125 MHz, CD$_2$Cl$_2$) δ=219.6, 169.9, 150.8, 149.8, 144.8, 109.8, 76.1, 74.4, 72.8, 60.9, 60.8, 54.6, 43.2, 38.8, 36.0, 31.6, 31.4, 30.1, 28.9, 22.3, 22.2, 20.5, 19.6, 16.7, 15.0, 13.6 ppm; HRMS (ESI-TOF) calcd for C$_{26}$H$_{41}$N$_3$O$_6^+$ [M+H$^+$] 492.3068, found 492.3069.

Epothilone Compound 10:

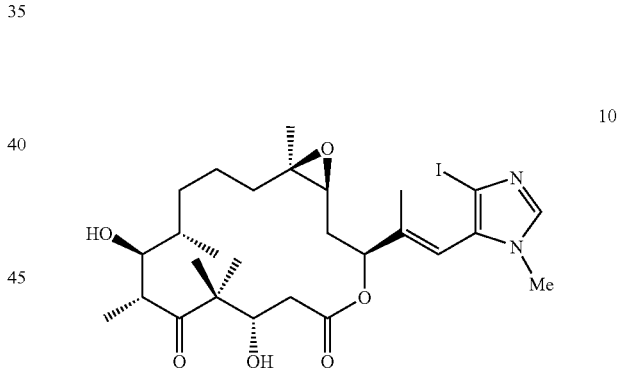

Method A; white foam; 43% yield; $R_f$=0.26 (silica gel, EtOAc); $[\alpha]_D^{32}$=−31.5 (DMSO, c=0.20); IR (film) $u_{max}$ 3472 br, 3201, 2919, 2355, 1725, 1684, 1461, 1378, 1249, 1149, 1061, 985, 732, 667 cm$^{-1}$; $^1$H NMR (500 MHz, C$_6$D$_6$) δ=6.46 (s, 1 H), 6.13 (s, 1 H), 5.43 (br s, 1 H), 5.26 (d, J=5.5 Hz, 1 H), 4.72 (d, J=10.6 Hz, 1 H), 3.86 (s, 1 H), 3.43 (dq, J=3.6, 6.8 Hz, 1 H), 2.78 (br s, 1 H), 2.74 (dd, J=5.4, 6.8 Hz, 1 H), 2.67 (s, 3 H), 2.56 (dd, J=11.1, 14.1 Hz, 1 H), 2.25 (dd, J=2.7, 14.1 Hz, 1 H), 1.94 (ddd, J=2.7, 4.6, 15.1 Hz, 1 H), 1.88-1.80 (m, 2H), 1.68-1.55 (m, 2 H), 1.51 (s, 3 H), 1.50-1.40 (m, 4 H), 1.36 (s, 3 H), 1.17 (s, 3 H), 1.16 (d, J=6.9 Hz, 3 H), 1.14 (s, 3 H), 1.00 ppm (d, J=7.0 Hz, 3 H); $^{13}$C NMR (125 MHz, C$_6$D$_6$) δ=220.2, 170.1, 145.1, 128.3, 113.4, 112.3, 106.1, 75.9, 74.0, 71.6, 61.6, 60.9, 54.4, 42.7, 39.7, 36.7, 32.2, 31.9, 30.4, 30.2, 22.9, 22.8, 22.3, 17.9, 16.8, 13.4, 11.8 ppm; HRMS (ESI-TOF) calcd for C$_{27}$H$_{41}$N$_2$O$_6^+$ [M+H$^+$] 617.2082, found 617.2081.

Epothilone Compound 11:

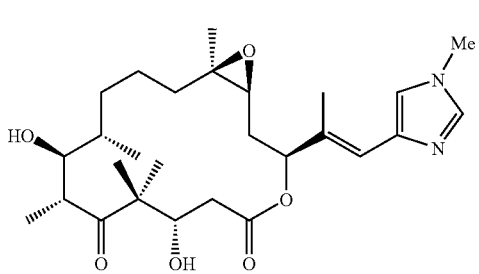

11

Method A; colorless film; 68% yield; $R_f$=0.10 (silica gel, EtOAc:acetone, 9:1); $[α]_D^{32}$=−15.4 (CH$_2$Cl$_2$, c=0.13); IR (film) u$_{max}$ 3384 br, 2925, 2345, 1724, 1718, 1685, 1654, 1560, 1458, 1376, 1256, 1143, 1053, 979, 702, 620 cm$^{-1}$; $^1$H NMR (500 MHz, CD$_2$Cl$_2$) δ=7.42 (s, 1 H), 6.89 (s, 1 H), 6.42 (s, 1 H), 5.38-5.33 (m, 1 H), 4.26 (dd, J=2.4, 10.5 Hz, 1 H), 3.70 (t, J=4.5 Hz, 1 H), 3.68 (s, 3 H), 3.61 (br s, 1H), 3.30-3.23 (m, 1 H), 2.76 (dd, J=3.7, 8.3 Hz, 1 H), 2.65 (br s, 1 H), 2.46 (dd, J=10.6, 14.1 Hz, 1 H), 2.29 (dd, J=2.9, 14.3 Hz, 1 H), 2.20-2.05 (m, 1 H), 1.99 (s, 3 H), 1.91-1.83 (m, 1 H), 1.74-1.65 (m, 2 H), 1.52-1.45 (m, 1 H), 1.46-1.30 (m, 4 H), 1.35 (s, 3 H), 1.25 (s, 3 H), 1.14 (d, J=6.8 Hz, 3 H), 1.03 (s, 3 H), 0.99 ppm (d, J=7.0 Hz, 3H); $^{13}$C NMR (150 MHz, CD$_2$Cl$_2$) δ=220.8, 170.6, 140.2, 137.4, 134.7, 119.3, 118.1, 77.0, 73.8, 72.0, 62.6, 61.6, 54.2, 42.6, 39.8, 36.7, 32.9, 31.1, 31.1, 30.0, 22.6, 22.4, 18.6, 17.9, 17.1, 15.9, 13.4 ppm; HRMS (ESI-TOF) calcd for C$_{27}$H$_{42}$N$_2$O$_6$$^+$ [M+H$^+$] 491.3115, found 491.3113.

Epothilone Compound 12:

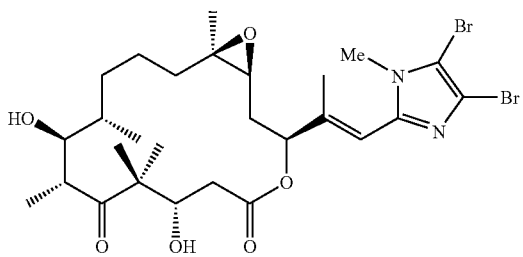

12

Method A; white foam; 76% yield; $R_f$=0.61 (silica gel, EtOAc:hexanes, 1:1); $[α]_D^{32}$=−20.6 (CH$_2$Cl$_2$, c=0.32); IR (film) u$_{max}$ 3436 br, 2919, 2849, 2355, 1731, 1684, 1461, 1384, 1249, 1220, 1143, 1067, 732, 662 cm$^{-1}$; $^1$H NMR (500 MHz, CDCl$_3$) δ=6.14 (s, 1H), 5.44 (dd, J=3.0, 6.5 Hz, 1 H), 4.26 (dd, J=3.0, 10.0 Hz, 1 H), 3.75 (t, J=4.5 Hz, 1 H), 3.44 (s, 3H), 3.35 (dq, J=4.5, 6.5 Hz, 1 H), 2.85 (t, J=6.0 Hz, 1 H), 2.56 (d, J=10.0 Hz, 1 H), 2.54 (d, J=10.0 Hz, 1 H), 2.40 (dd, J=2.5, 14.0 Hz, 1 H), 1.78 (s, 3 H), 1.75-1.63 (m, 1 H), 1.58-1.36 (m, 6 H), 1.37 (s, 3 H), 1.30 (s, 3 H), 1.26 (s, 3 H), 1.16 (d, J=7.0 Hz, 3 H), 1.79 (s, 3 H), 0.99 ppm (d, J=7.0 Hz, 3 H); $^{13}$C NMR (125 MHz, CD$_2$Cl$_2$) δ=220.8, 170.4, 143.9, 129.8, 118.7, 113.7, 111.6, 75.8, 74.2, 72.4, 61.4, 61.4, 53.3, 42.9, 39.1, 36.3, 31.9, 31.5, 30.4, 22.7, 22.2, 21.7, 19.1, 16.8, 16.4, 13.6 ppm; HRMS (ESI-TOF) calcd for C$_{27}$H$_{40}$Br$_2$N$_2$O$_6$$^+$[M+H$^+$] 647.1331, found 647.1309.

Epothilone Compound 13:

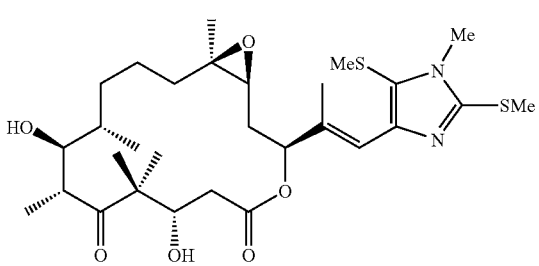

13

Method A; colorless film; 79% yield; $R_f$=0.38 (silica gel, EtOAc:hexanes, 1:1); $[α]_D^{32}$=+13.9 (DMSO, c=0.36); IR (film) u$_{max}$ 3444, br, 2956, 2926, 2359, 1732, 1682, 1455, 1378, 1314, 1250, 1146, 1092, 1047, 976, 885, 821, 662 cm$^{-1}$; $^1$H NMR (500 MHz, CDCl$_3$) δ=6.55 (s, 1 H), 5.45 (dd, J=2.7, 8.6 Hz, 1 H), 4.25 (d, J=9.5 Hz, 1 H), 3.77 (br s, 1 H), 3.56 (s, 3 H), 3.49 (br s, 1 H), 3.29 (dq, J=4.1, 6.8 Hz, 1H), 2.82 (dd, J=3.8, 8.5 Hz, 1 H), 2.70 (br s, 1H), 2.65 (s, 3 H), 2.53 (dd, J=10.3, 14.4 Hz, 1 H), 2.37 (dd, J=2.9, 14.4 Hz, 1 H), 2.28 (s, 3 H), 2.19 (s, 3 H), 2.29-2.14 (m, 1 H), 1.90 (td, J=8.6, 15.2 Hz, 1 H), 1.79-1.70 (m, 1 H), 1.68-1.46 (m, 6 H), 1.34 (s, 3 H), 1.28 (s, 3 H), 1.17 (d, J=6.9 Hz, 3 H), 1.09 (s, 3 H), 1.01 ppm (d, J=7.0 Hz, 3H); $^{13}$C NMR (150 MHz, CDCl$_3$) δ=220.5, 170.5, 145.6, 143.7, 135.7, 123.8, 116.1, 77.7, 73.7, 72.8, 62.0, 61.6, 53.1, 42.7, 39.4, 36.2, 32.7, 32.4, 30.9, 30.6, 22.6, 22.2, 21.9, 20.5, 19.4, 17.5, 15.2, 15.1, 13.3 ppm; HRMS (ESI-TOF) calcd for C$_{29}$H$_{46}$N$_2$O$_6$S$_2$$^+$ [M+H$^+$] 583.2870, found 583.2853.

Epothilone Compound 14:

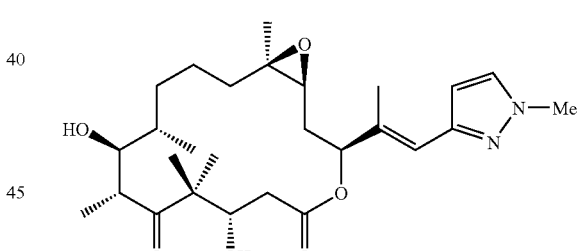

14

Method A; white solid; 71% yield; $R_f$=0.64 (silica gel, EtOAc); $[α]_D^{32}$=−14.0 (CH$_2$Cl$_2$, c=0.50); IR (film) u$_{max}$ 3446 br, 2966, 2936, 1732, 1688, 1508, 1455, 1378, 1251, 1143, 1049, 979, 761, 732, 697 cm$^{-1}$; $^1$H NMR (600 MHz, CDCl$_3$) δ=7.33 (s, 1 H), 6.53 (s, 1H), 6.30 (s, 1 H), 5.44 (dd, J=2.9, 7.2 Hz, 1 H), 4.19 (d, J=8.0 Hz, 1 H), 3.90 (s, 3 H), 3.79 (t, J=4.2 Hz, 1 H), 3.33-3.27 (m, 1 H), 2.81 (dd, J=5.0, 7.2 Hz, 1 H), 2.55 (dd, J=10.2, 14.2 Hz, 1H), 2.38 (dd, J=2.7, 14.1 Hz, 1 H), 2.01 (td, J=4.2, 15.0 Hz, 1 H), 2.04 (s, 3 H), 1.92 (td, J=7.5, 15.0 Hz, 1 H), 1.77-1.67 (m, 1 H), 1.58-1.38 (m, 6 H), 1.36 (s, 3 H), 1.27 (s, 3 H), 1.17 (d, J=6.8 Hz, 3 H), 1.08 (s, 3 H), 1.00 ppm (d, J=6.8 Hz, 3 H); $^{13}$C NMR (125 MHz, C$_6$D$_6$:CD$_3$OD, 3:1) δ=219.8, 171.0, 149.5, 137.2, 131.5, 118.3, 106.2, 77.2, 76.0, 72.1, 62.5, 62.0, 54.0, 44.7, 39.7, 38.1, 36.6, 33.0, 32.5, 30.3, 23.3, 22.4, 21.1, 19.4, 17.8, 15.3, 14.0 ppm; HRMS (ESI-TOF) calcd for C$_{27}$H$_{42}$N$_2$O$_6$$^+$ [M+H$^+$] 491.3115, found 491.3109.

Epothilone Compound 15:

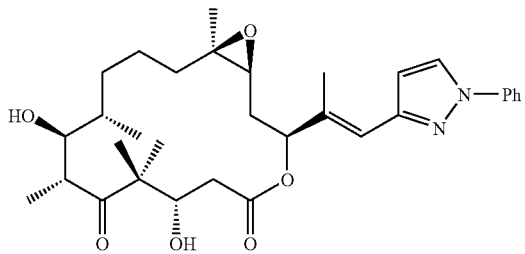

Method A; white solid; 66% yield; $R_f$=0.73 (silica gel, EtOAc:hexanes, 1:1); $[\alpha]_D^{32}$=−28.3 (CH$_2$Cl$_2$, c=0.60); IR (film) u$_{max}$ 3460 br, 2955, 2919, 1731, 1684, 1596, 1513, 1455, 1373, 1255, 1143, 1049, 973, 756 cm$^{-1}$; $^1$H NMR (600 MHz, CDCl$_3$) δ=7.90 (s, 1H), 7.68 (d, J=7.9 Hz, 2 H), 7.45 (t, J=7.7 Hz, 2H), 7.29 (d, J=7.4 Hz, 1 H), 6.61 (s, 1 H), 6.52 (s, 1 H), 5.50-5.47 (m, 1 H), 4.19 (d, J=7.9 Hz, 1 H), 3.91, (br s, 1 H), 3.80 (t, J=3.9 Hz, 1 H), 3.36-3.30 (m, 1 H), 2.83 (t, J=6.3 Hz, 1 H), 2.58 (dd, J=10.1, 14.0 Hz, 1 H), 2.50 (br s, 1 H), 2.42 (dd, J=2.6, 14.1 Hz, 1 H), 2.14 (s, 3 H), 2.12-2.06 (m, 1 H), 1.97 (dt, J=7.2, 14.7 Hz, 1 H), 1.79-1.66 (m, 1 H), 1.58-1.40 (m, 6 H), 1.37 (s, 3 H), 1.27 (s, 3 H), 1.17 (d, J=6.8 Hz, 3 H), 1.09 (s, 3 H), 1.01 ppm (d, J=6.9 Hz, 3 H); $^{13}$C NMR (150 MHz, CDCl$_3$) δ=220.7, 170.6, 150.3, 139.9, 137.0, 129.4, 127.4, 126.5, 119.0, 118.2, 108.2, 74.4, 73.4, 61.4, 61.2, 52.7, 43.3, 39.0, 36.5, 32.0, 31.8, 30.7, 22.9, 22.7, 21.1, 20.6, 17.2, 15.8, 13.9 ppm; HRMS (ESI-TOF) calcd for C$_{32}$H$_{44}$N$_2$O$_6{}^+$ [M+H$^+$] 553.3272, found 553.3263.

Epothilone Compound 16:

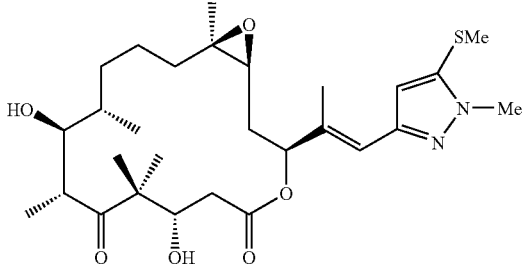

Method A; white solid; 60% yield; $R_f$=0.82 (silica gel, EtOAc); $[\alpha]_D^{32}$=−28.3 (CH$_2$Cl$_2$, c=0.53); IR (film) u$_{max}$ 3444 br, 2966, 2931, 1738, 1732, 1694, 1682, 1469, 1455, 1381, 1371, 1284, 1266, 1250, 1148, 1056, 978, 736 cm$^{-1}$; $^1$H NMR (600 MHz, CD$_2$Cl$_2$) δ=6.41 (s, 1H), 6.33 (s, 1 H), 5.38 (dd, J=2.3, 8.12 Hz, 1 H), 4.20-4.15 (m, 1 H), 3.84 (s, 3 H), 3.72 (dd, J=4.0, 7.8 Hz, 1 H), 3.67 (d, J=5.6 Hz, 1 H), 3.29-3.24 (m, 1 H), 2.77 (dd, J=4.3, 7.9 Hz, 1H), 2.51 (br s, 1 H), 2.48 (dd, J=10.3, 14.3 Hz, 1H), 2.41 (s, 3 H), 2.36-2.32 (m, 1 H), 2.09-2.03 (m, 1 H), 2.01 (s, 3 H), 1.94-1.86 (m, 1 H), 1.72-1.65 (m, 1 H), 1.53-1.35 (m, 6 H), 1.34 (s, 3 H), 1.25 (s, 3 H), 1.14 (d, J=6.8 Hz, 3 H), 1.04 (s, 3H), 0.99 ppm (d, J=7.0 Hz, 3 H); $^{13}$C NMR (151 MHz, CD$_2$Cl$_2$) δ=220.7, 170.5, 148.1, 137.2, 136.4, 118.1, 108.9, 76.7, 74.3, 73.2, 61.5, 61.2, 52.8, 43.1, 39.0, 36.5, 32.1, 31.9, 30.7, 22.8, 22.6, 21.2, 20.3, 18.8, 17.1, 15.7, 14.2, 13.9 ppm; HRMS (ESI-TOF) calcd for C$_{28}$H$_{44}$N$_2$O$_6$S$^+$ [M+H$^+$] 537.2993, found 537.2992.

Epothilone Compound 17:

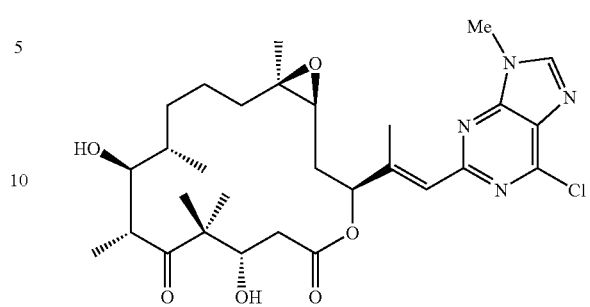

Method A; colorless film; 52% yield; $R_f$=0.34 (silica gel, EtOAc); $[\alpha]_D^{32}$=−33.9 (CH$_2$Cl$_2$, c=0.12); IR (film) u$_{max}$ 3418 br, 2928, 1732, 1688, 1599, 1556, 1395, 1342, 1262, 1148, 1055, 981, 906, 736 cm$^{-1}$; $^1$H NMR (500 MHz, CD$_2$Cl$_2$) δ=8.07 (s, 1 H), 6.69 (s, 1 H), 6.23 (q, J=5.7 Hz, 1 H), 5.42 (dd, J=1.5, 8.5 Hz, 1 H), 4.36-4.30 (m, 1 H), 3.88 (s, 3 H), 3.73 (dd, J=4.2, 4.6 Hz, 1 H), 2.81 (dd, J=4.2, 8.0 Hz, 1 H), 2.53 (dd, J=10.6, 13.9 Hz, 1 H), 2.38 (s, 3 H), 2.38-2.35 (m, 1 H), 2.21-2.12 (m, 1 H), 1.98-1.901 (m, 1 H), 1.75-1.67 (m, 1 H), 1.49-1.28 (m, 6 H), 1.41 (s, 3 H), 1.27 (s, 3 H), 1.17 (d, J=6.8 Hz, 3 H), 1.06 (s, 3 H), 1.00 ppm (d, J=7.0 Hz, 3 H); $^{13}$C NMR (151 MHz, CD$_2$Cl$_2$) δ=219.7, 170.0, 158.5, 152.3, 149.5, 146.7, 145.4, 128.7, 122.8, 76.3, 73.7, 72.3, 61.4, 61.0, 52.9, 42.4, 39.0, 36.0, 32.1, 31.7, 30.3, 29.8, 22.1, 21.9, 21.3, 18.4, 16.5, 15.6, 13.0 ppm; HRMS (ESI-TOF) calcd for C$_{29}$H$_{41}$ClN$_4$O$_6{}^+$ [M+H$^+$] 577.2787, found 577.2789.

Epothilone Compound 18:

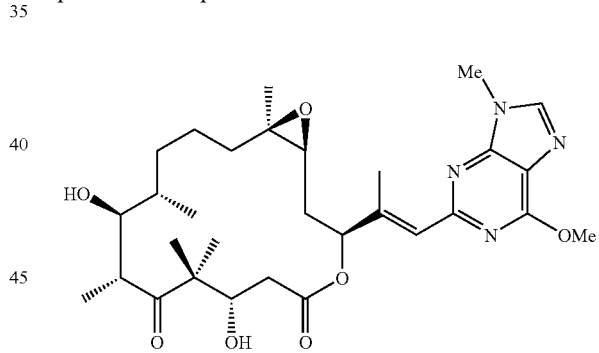

Method A; white solid; 39% yield; $R_f$=0.23 (silica gel, EtOAc); $[\alpha]_D^{32}$=−13.4 (CH$_2$Cl$_2$, c=3.5); IR (film) u$_{max}$ 3401 br, 2943, 1731, 1684, 1590, 1572, 1461, 1390, 1243, 1073. 1055, 979, 726 cm$^{-1}$; $^1$H NMR (500 MHz, CDCl$_3$) δ=7.78 (s, 1H), 6.52 (s, 1 H), 5.34 (d, J=7.0 Hz, 1 H), 4.26 (d, J=9.5 Hz, 1 H), 4.20 (br s, 1 H), 4.09 (s, 3 H), 3.76 (s, 3 H), 3.68 (s, 1 H), 3.26-3.20 (m, 1 H), 2.73 (dd, J=4.0, 7.6 Hz, 1 H), 2.67 (br s, 1 H), 2.49 (dd, J=10.6, 13.5 Hz, 1 H), 2.31 (s, 3 H), 2.30-2.26 (m, 1 H), 2.09 (d, J=15.3 Hz, 1 H), 1.88-1.81 (m, 1 H), 1.71-1.60 (m, 1 H), 1.49-1.39 (m, 2 H), 1.38-1.24 (m, 4 H), 1.32 (s, 3 H), 1.20 (s, 3 H), 1.09 (d, J=6.8 Hz, 3 H), 1.00 (s, 3 H), 0.92 ppm (d, J=6.9 Hz, 3 H); $^{13}$C NMR (150 MHz, CDCl$_3$) δ=220.5, 170.5, 160.2, 158.7, 152.4, 145.3, 142.8, 128.3, 124.1, 76.8, 73.8, 72.8, 61.9, 61.5, 54.4, 53.4, 42.6, 39.6, 36.2, 32.5, 31.9, 30.7, 30.0, 22.7, 22.1, 21.9, 19.1, 17.0, 16.3, 13.4 ppm; HRMS (ESI-TOF) calcd for C$_{30}$H$_{44}$N$_4$O$_7{}^+$ [M+H$^+$] 573.3283, found 573.3278.

Epothilone Compound 19:

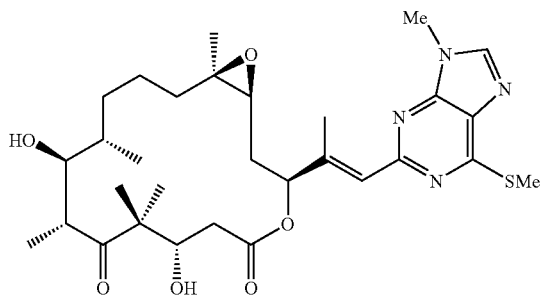

Method A; white solid; 53% yield; $R_f$=0.42 (silica gel, EtOAc); $[\alpha]_D^{32}$=−29 (CH$_2$Cl$_2$, c=0.059); IR (film) $u_{max}$ 3444 br, 2923, 1732, 1565, 1556, 1454, 1384, 1336, 1259, 1056, 797, 736 cm$^{-1}$; $^1$H NMR (600 MHz, CD$_2$Cl$_2$) δ=7.92 (s, 1 H), 6.64 (s, 1 H), 5.41 (d, J=7.4 Hz, 1 H), 4.35 (dd, J=2.3, 10.4 Hz, 1H), 4.12 (br s, 1 H), 3.81 (s, 3 H), 3.73 (t, J=4.5 Hz, 1 H), 3.33-3.27 (m, 1 H), 3.08 (br s, 1 H), 2.82 (dd, J=3.8, 8.2 Hz, 1 H), 2.72 (s, 3H), 2.53 (dd, J=10.6, 14.0 Hz, 1 H), 2.40 (s, 3 H), 2.44-2.33 (m, 1 H), 2.21-2.15 (m, 1 H), 1.98-1.90 (m, 1 H), 1.76-1.68 (m, 1 H), 1.54-1.47 (m, 2 H), 1.46-1.22 (m, 4 H), 1.40 (s, 3 H), 1.27 (s, 3 H), 1.16 (d, J=6.8 Hz, 3 H), 1.06 (s, 3 H), 1.01 ppm (d, J=7.0 Hz, 3 H); $^{13}$C NMR (150 MHz, CD$_2$Cl$_2$) δ=220.1, 170.1, 160.3, 158.6, 148.8, 145.3, 143.4, 128.7, 124.0, 76.9, 73.6, 72.2, 61.8, 61.5, 53.2, 42.3, 39.3, 36.0, 32.4, 32.3, 30.4, 29.4, 22.2, 21.9, 21.7, 18.1, 16.6, 15.9, 12.8, 11.7 ppm; HRMS (ESI-TOF) calcd for C$_{30}$H$_{44}$N$_4$O$_6$S$^+$ [M+H$^+$] 589.3054, found 589.3056.

Epothilone Compound 20:

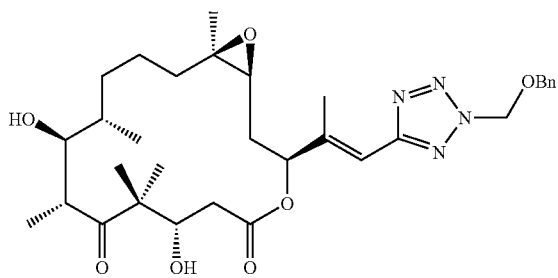

Method A; white solid; 56% yield; $R_f$=0.39 (silica gel, EtOAc:hexanes, 1:1); $[\alpha]_D^{32}$=−23.1 (CD$_2$Cl$_2$, c=9.0); IR (film) $u_{max}$ 3446 br, 2933, 2366, 1734, 1684, 1458, 1381, 1251, 1100, 746, 699 cm$^{-1}$; $^1$H NMR (600 MHz, CD$_2$Cl$_2$) δ=7.38-7.30 (m, 5 H), 6.69 (s, 1 H), 5.92 (s, 2 H), 5.50 (dd, J=3.0, 6.1 Hz, 1H), 4.67 (s, 2 H), 4.16-4.11 (m, 1 H), 3.73 (s, 1H), 3.47 (d, J=5.9 Hz, 1 H), 3.34-3.27 (m, 1 H), 2.80 (t, J=6.2 Hz, 1 H), 2.56 (dd, J=10.1, 14.3 Hz, 1 H), 2.44 (dd, J=3.4, 14.4 Hz, 1 H), 2.35 (br s, 1 H), 2.28 (s, 3 H), 2.10-1.97 (m, 2 H), 1.71-1.64 (m, 1 H), 1.71-1.64 (m, 6 H), 1.36 (s, 3 H), 1.27 (s, 3 H), 1.15 (d, J=6.8 Hz, 3 H), 1.05 (s, 3H), 0.99 ppm (d, J=6.9 Hz, 3 H); $^{13}$C NMR (150 MHz, CD$_2$Cl$_2$) δ=219.8, 170.0, 163.4, 144.7, 135.6, 128.2 (2C), 128.0, 127.8 (2C), 111.2, 79.4, 75.7, 74.5, 73.2, 71.7, 60.7, 60.6, 52.2, 43.4, 38.6, 36.0, 31.3 (2C), 30.0, 22.4, 22.3, 20.2, 16.7 (2C), 15.8, 13.8 ppm; HRMS (ESI-TOF) calcd for C$_{32}$H$_{46}$N$_4$O$_7^+$ [M+H$^+$] 599.3439, found 599.3432.

Epothilone Compound 21:

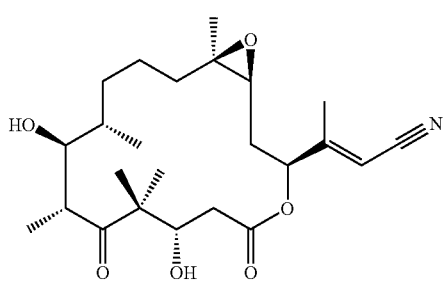

Method B; colorless film; 34% yield; $R_f$=0.24 (silica gel, EtOAc:hexanes, 1:1); $[\alpha]_D^{32}$=−15.4 (CH$_2$Cl$_2$, c=0.14); IR (film) $u_{max}$ 3460 br, 2919, 2849, 1731, 1684, 1449, 1378, 1255, 1143, 1073, 726 cm$^{-1}$; $^1$H NMR (500 MHz, CDCl$_3$) δ=5.55 (s, 1 H), 5.48 (t, J=4.0 Hz, 1 H), 4.11 (dd, J=3.1, 10.1 Hz, 1 H), 3.76 (dd, J=3.4, 5.1 Hz, 1 H), 3.68 (br s, 1 H), 3.37-3.34 (m, 1 H), 2.68 (t, J=6.2 Hz, 1 H), 2.55 (dd, J=10.2, 14.1 Hz, 1 H), 2.47 (dd, J=3.5, 14.2 Hz, 1H), 2.12 (s, 3 H), 1.99-1.94 (m, 1 H), 1.70-1.20 (m, 9 H), 1.37 (s, 3 H), 1.30 (s, 3 H), 1.16 (d, J=6.9 Hz, 3 H), 1.06 (s, 3 H), 0.98 ppm (d, J=6.9 Hz, 3 H); $^{13}$C NMR (126 MHz, CDCl$_3$) δ=220.1, 170.0, 159.3, 97.3, 77.2, 73.8, 73.6, 60.7, 60.0, 52.4, 44.0, 38.3, 36.1, 31.0, 30.5, 29.9, 29.7, 23.1, 22.7, 21.4, 19.8, 18.2, 17.3, 14.6 ppm; HRMS (ESI-TOF) calcd for C$_{24}$H$_{37}$NO$_6^+$ [M+Na$^+$] 458.2513, found 458.2504.

Tosylate Compound 24:

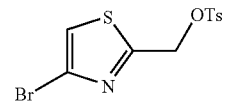

To a solution of alcohol Compound 23 (1.23 g, 6.34 mmol), p-toluensulfonyl chloride (1.81 g, 9.48 mmol, 1.0 equiv.), and DMAP (10.0 mg, 82 μmol, 0.0086 equiv.) in CH$_2$Cl$_2$ (50 mL) was added NEt$_3$ (2.67 mL, 19.02 mmol, 2.0 equiv.) at zero ° C. The reaction mixture was stirred zero ° C. for 15 minutes, quenched with saturated aqueous NH$_4$Cl solution (40 mL) and extracted with CH$_2$Cl$_2$ (3×25 mL). The combined organic layers were washed with brine (30 mL), dried (Na$_2$SO$_4$) and concentrated in vacuo. Purification of the residue by flash column chromatography (silica gel, EtOAc:hexanes, 1:3) afforded tosylate Compound 24 (1.86 g, 84% yield) as a white powder.

Compound 24: $R_f$=0.51 (silica gel, EtOAc:hexanes, 1:3); IR (film) $u_{max}$ 3121, 1597, 1482, 1368, 1190, 1176, 1093, 951, 890, 814, 665, 552 cm$^{-1}$; $^1$H NMR (500 MHz, CDCl$_3$) δ=7.83-7.79 (m, 2 H), 7.37-7.33 (m, 2 H), 7.26 (s, 1 H), 5.28 (s, 2 H), 2.46 ppm (s, 3 H); $^{13}$C NMR (100 MHz, CD$_2$Cl$_2$) δ=163.5, 145.9, 132.2, 130.0, 128.1, 125.3, 119.0, 66.9, 21.7 ppm; HRMS (ESI-TOF) calcd for C$_{11}$H$_{10}$BrNO$_3$S$_2^+$ [M+Na$^+$] 369.9178, found 369.9176.

Thiazole Compound 25a:

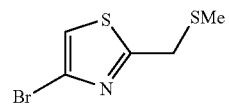

A solution of tosylate Compound 24 (260 mg, 0.75 mmol, 1.0 equiv.) and sodium thiomethoxide (205 mg, 2.24 mmol, 3.0 equiv.) in absolute EtOH (20 mL) was stirred at 25° C. for 1 hour. The reaction was quenched with saturated aqueous NH$_4$Cl solution (10 mL) and H$_2$O (20 mL), and extracted with EtOAc (3×15 mL). The combined organic layers were washed with brine (20 mL), dried (MgSO$_4$) and concentrated in vacuo. Purification of the residue pre-adsorbed onto silica by flash column chromatography (silica gel, EtOAc:hexanes, 1:4) afforded Compound 25a (162 mg, 97% yield) as a yellow oil.

Compound 25a: R$_f$=0.56 (silica gel, EtOAc:hexanes, 1:4); IR (film) u$_{max}$ 3118, 2915, 1473, 1433, 1404, 1255, 1204, 1114, 1074, 982, 889, 834, 734 cm$^{-1}$; $^1$H NMR (500 MHz, CDCl$_3$) δ=7.18 (s, 1 H), 3.93 (s, 2 H), 2.12 ppm (s, 3 H); $^{13}$C NMR (100 MHz, CD$_2$Cl$_2$) δ=170.9, 124.1, 117.7, 35.3, 15.7 ppm; HRMS (ESI-TOF) calcd for C$_5$H$_6$BrNS$_2^+$ [M+H$^+$] 223.9198, found 223.9194.

Thiazole Compound 25b:

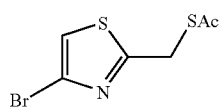

To a solution of tosylate Compound 24 (513 mg, 1.47 mmol, 1.0 equiv.) in CH$_2$Cl$_2$ (40 mL) at zero ° C. was added NEt$_3$ (163 mg, 1.62 mmol, 1.1 equiv.) and thioacetic acid (123 mg, 1.62 mmol, 1.1 equiv.). The reaction solution was permitted to warm to 25° C. over a period of 1 hour. The reaction was then quenched with saturated aqueous NH$_4$Cl solution (30 mL) and extracted with CH$_2$Cl$_2$ (3×15 mL). The combined organic layers were washed with brine (20 mL), dried (MgSO$_4$) and concentrated in vacuo. Purification of the residue by flash column chromatography (silica gel, EtOAc:hexanes, 1:5) afforded thioacetate Compound 25b (283 mg, 78% yield) as a yellow oil.

Compound 25b: R$_f$=0.48 (silica gel, EtOAc:hexanes, 1:4); IR (film) u$_{max}$ 3443, 2919, 1694, 1472, 1256, 1130, 1072, 955, 893, 836 cm$^{-1}$; $^1$H NMR (500 MHz, CDCl$_3$) δ=7.15 (s, 1 H), 4.41 (s, 2 H), 2.40 ppm (s, 3 H); $^{13}$C NMR (125 MHz, CDCl$_3$) δ=193.9, 167.9, 124.5, 117.9, 30.4, 30.2 ppm; HRMS (ESI-TOF) calcd for C$_6$H$_6$BrNOS$_2^+$ [M+Na$^+$] 273.8996, found 273.8968.

Stannane Compound 26a:

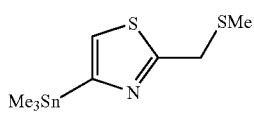

A solution of bromide 25a (26 mg, 0.12 mmol, 1.0 equiv.), hexamethylditin (266 mg, 0.81 mmol, 6.75 equiv.), Pd(PPh$_3$)$_4$ (13.4 mg, 11.6 μmol, 0.1 equiv.) in toluene (5 mL) was heated to 110° C. for 1 hour. The reaction was cooled to 25° C. and concentrated in vacuo. Purification of the residue by flash column chromatography (NEt$_3$ prewashed silica gel, EtOAc:hexanes, 1:10) afforded stannane Compound 26a (34 mg, 95% yield) as a colorless oil. 26a: R$_f$=0.59 (silica gel, EtOAc:hexanes, 1:5); IR (film) u$_{max}$ 2916, 2359, 1456, 1384, 1072, 771, 531 cm$^{-1}$; $^1$H NMR (400 MHz, CDCl$_3$) δ=7.33 (s, 1 H), 4.07 (s, 2 H), 2.16 (s, 3 H), 0.35 ppm (s, 9 H); $^{13}$C NMR (150 MHz, CDCl$_3$) δ=169.6, 159.4, 126.5, 34.9, 15.7, −8.9 ppm; HRMS (ESI-TOF) calcd for C$_8$H$_{15}$NS$_2$Sn$^+$ [M+H$^+$] 309.9741, found 309.9729.

Stannane Compound 26b:

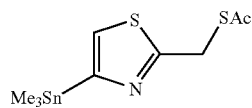

A solution of bromide Compound 25a (245 mg, 0.97 mmol, 1.0 equiv.), hexamethylditin (2.2 g, 6.81 mmol, 7.0 equiv.), Pd(PPh$_3$)$_4$ (225 mg, 0.19 mmol, 0.2 equiv.) in toluene (7 mL) was heated to 110 C for 1 hour. The reaction was cooled to 25° C. and concentrated in vacuo. Purification of the residue by flash column chromatography (NEt$_3$ prewashed silica gel, EtOAc:hexanes, 1:10) afforded stannane Compound 26b (212 mg, 63% yield) as a yellow oil.

Compound 26b: R$_f$=0.70 (silica gel, EtOAc:hexanes, 1:5); IR (film) u$_{max}$ 2982, 2915, 1694, 1455, 1354, 1133, 1073, 958, 772, 622, 532 cm$^{-1}$; $^1$H NMR (400 MHz, CDCl$_3$) δ=7.28 (s, 1 H), 4.51 (s, 2 H), 2.37 (s, 3 H), 0.33 ppm (s, 9 H); $^{13}$C NMR (150 MHz, CDCl$_3$) δ=194.1, 166.9, 159.7, 126.7, 30.2, 30.1, −8.9 ppm; HRMS (ESI-TOF) calcd for C$_9$H$_{15}$NOS$_2$Sn$^+$ [M+H$^+$] 337.9690, found 337.9687.

Stannane Compound 28:

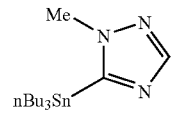

To a solution of n-BuLi (2.15 M in THF, 230 μL, 0.50 mmol, 1.0 equiv.) in THF (5 mL) at −78 C was added dropwise methylcyclohexane (5 mL) followed by a solution of 1-methyl-1,2,4-triazole Compound 27 (420 mg, 0.50 mmol, 1.0 equiv.) in THF (5 mL). The reaction mixture was stirred for 10 hours at −78° C. and quenched with n-Bu$_3$SnCl (135 μL, 0.50 mmol, 1.0 equiv.). The salts were then filtered under an inert atmosphere and the product was distilled under reduced pressure (140° C./1 mm Hg). Stannane Compound 28 (154 mg, 83% yield) was obtained as a white oil.

Compound 28: IR (film) u$_{max}$ 3425, 2954, 2919, 1632, 1537, 1462, 1376, 1303, 1270, 1157, 1074, 994, 960, 875, 698 cm$^{-1}$; $^1$H NMR (400 MHz, C$_6$D$_6$) δ=8.19 (s, 3 H), 3.45 (s, 3 H), 1.65-1.45 (m, 6 H), 1.36-1.16 (m, 6 H), 1.15-1.05 (m, 6 H), 0.86 ppm (t, J=7.6 Hz, 9 H); $^{13}$C NMR (100 MHz, CDCl$_3$) δ=158.0, 153.0, 36.7, 29.2, 27.7, 14.0, 10.7 ppm; HRMS (ESI-TOF) calcd for C$_{15}$H$_{31}$N$_3$Sn$^+$ [M+H$^+$] 374.1613, found 374.1611.

Iodide Compounds 29a and 29b:

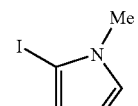

29a

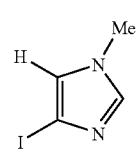

29b

Iodide Compounds 29a and 29b were prepared according to literature procedures. [Lovely et al., *Heterocycles* 2003, 60, 1; Carver et al., *Tetrahedron* 1996, 44, 1831.]

Stannane Compound 30a:

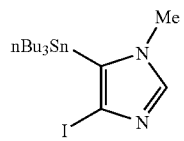

To a solution of iodide Compound 29a (400 mg, 1.20 mmol, 1.0 equiv.) in THF (10 mL) was added EtMgBr (3.0 M in THF, 400 µL, 1.20 mmol, 1.0 equiv.) at 25° C. After stirring at 25° C. for 1.5 hour, n-Bu₃SnCl (325 µL, 1.20 mmol, 1.0 equiv.) was added and the reaction mixture was stirred for an additional 6 hours. The reaction was then quenched with saturated aqueous NH₄Cl solution (20 mL) and extracted with EtOAc (3×15 mL). The combined organic layers were washed with brine (20 mL), dried (Na₂SO₄) and concentrated in vacuo. Purification of the residue by flash column chromatography (NEt₃ prewashed silica gel, EtOAc:hexanes, 3:7) afforded stannane Compound 30a (441 mg, 74% yield) as a colorless oil.

Compound 30a: $R_f$=0.42 (silica gel, EtOAc:hexanes, 6:4); IR (film) $u_{max}$ 3448, 2953, 2920, 2850, 1636, 1459, 1420, 1375, 1226, 1158, 1074, 941, 664 cm$^{-1}$; $^1$H NMR (600 MHz, C₆D₆) δ=7.34 (s, 1H), 3.01 (s, 3 H), 1.85-1.51 (m, 6 H), 1.55-1.36 (m, 6H), 1.35-1.15 (m, 6 H), 1.06 ppm (t, J=7.5 Hz, 9 H); $^{13}$C NMR (125 MHz, C₆D₆) δ=142.9, 135.0, 97.1, 34.8, 29.6, 27.8, 14.0, 11.5 ppm; HRMS (ESI-TOF) calcd for C₁₆H₃₁I₁N₂Sn⁺ [M+H⁺] 499.0627, found 499.0633.

Stannane Compound 30b:

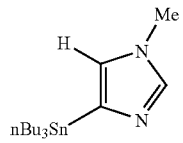

To a solution of iodide Compound 29b (219 mg, 1.05 mmol, 1.0 equiv.) in THF (5 mL) was added EtMgBr (1.1 M in THF, 0.96 mL, 1.05 mmol, 1.0 equiv.) at 25° C. After stirring at 25° C. for 1.5 hours, n-Bu₃SnCl (0.29 mL, 1.05 mmol, 1.0 equiv.) was added and stirred an additional 18 hours. The reaction was quenched with saturated aqueous NH₄Cl solution (20 mL) and extracted with EtOAc (3×15 mL). The combined organic layers were washed with brine (20 mL), dried (Na₂SO₄) and concentrated in vacuo. Purification of the residue by flash column chromatography (NEt₃ prewashed silica gel, EtOAc:hexanes, 2:1) afforded stannane Compound 30b (309 mg, 79% yield) as a colorless oil.

Compound 30b: $R_f$=0.30 (silica gel, EtOAc:hexanes, 2:1); IR (film) $u_{max}$ 2955, 2925, 2870, 2852, 1518, 1463, 1417, 1376, 1218, 1180, 1102, 680, 617 cm$^{-1}$; $^1$H NMR (600 MHz, C₆D₆) δ=7.24 (s, 1 H), 6.57 (s, 1 H), 2.68 (s, 3 H), 1.83-1.69 (m, 6 H), 1.47-1.39 (m, 6 H), 1.27-1.14 (m, 6 H), 0.93 ppm (t, J=7.4 Hz, 9 H); $^{13}$C NMR (125 MHz, C₆D₆) δ=140.6, 140.3, 127.9, 31.7, 29.7, 27.8, 14.0, 10.2 ppm; HRMS (ESI-TOF) calcd for C₁₆H₃₂N₂Sn⁺ [M+H⁺] 373.1660, found 373.1671.

Stannane Compound 32:

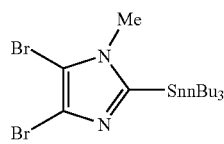

To a solution of tribromide Compound 31 (495 mg, 1.56 mmol, 1.0 equiv.) in THF (10 mL) at 25 C was added EtMgBr (3 M in THF, 520 µL, 1.56 mmol, 1.0 equiv.). After 5 minutes, n-Bu₃SnCl (420 µL, 1.56 mmol, 1.0 equiv.) was added and the reaction mixture was stirred for 1 hour. The reaction mixture was then quenched with saturated aqueous NH₄Cl solution (10 mL) and extracted with EtOAc (3×10 mL). The combined organic layers were washed with brine (15 mL), dried (Na₂SO₄) and concentrated in vacuo. Purification of the residue by flash column chromatography (NEt₃ prewashed silica gel, Et₂O:hexanes, 5:95) afforded stannane Compound 32 (710 mg, 86% yield) as a yellow oil.

Compound 32: $R_f$=0.6 (silica gel, EtOAc:hexanes, 2:8; IR (film) $u_{max}$ 3436, 2919, 2843, 2849, 1453, 1355, 1197, 1108, 1073, 867, 667 cm$^{-1}$; $^1$H NMR (500 MHz, C₆D₆) δ=2.87 (s, 3 H), 1.44-1.54 (m, 6 H), 1.36-1.24 (m, 6 H), 1.12-1.06 (m, 6 H), 0.88 ppm (t, J=7.5 Hz, 9 H); $^{13}$C NMR (100 MHz, C₆D₆) δ=133.6, 127.3, 121.1, 35.6, 29.2, 27.5, 13.8, 11.1 ppm; HRMS (ESI-TOF) calcd for C₁₆H₃₀Br₂N₂Sn⁺ [M+H⁺] 528.9870, found 528.9853.

Stannane Compound 33:

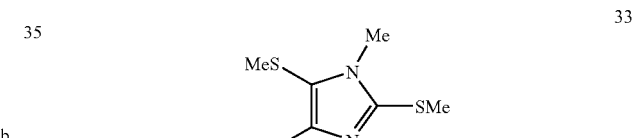

To a solution of tribromide Compound 31 (165 mg, 0.52 mmol, 1.0 equiv.) in THF (5 mL) at −78° C. was added n-BuLi (2.15 M in THF, 0.24 mL, 0.52 mmol, 1.0 equiv.). After 5 minutes, (MeS)₂ (47 µL, 0.52 mmol, 1.0 equiv.) was added and the reaction mixture was stirred for 5 minutes at the same temperature. A second aliquot of n-BuLi (2.15 M in THF, 0.24 mL, 0.52 mmol, 1.0 equiv.) was added. After 15 min, (MeS)₂ (47 µL, 0.52 mmol, 1.0 equiv.) was added and the reaction mixture was stirred for a further 5 minutes. A third aliquot of n-BuLi (2.15 M in THF, 0.24 mL, 0.52 mmol, 1.0 equiv.) was then added. After 15 minutes, n-Bu₃SnCl (140 µL, 0.52 mmol, 1.0 equiv.) was added and the reaction mixture was stirred for 1 hour. The reaction was quenched with saturated aqueous NH₄Cl solution (10 mL) and extracted with EtOAc (3×10 mL). The combined organic layers were washed with brine (15 mL), dried (Na₂SO₄) and concentrated in vacuo. Purification of the residue by flash column chromatography (NEt₃ prewashed silica gel, EtOAc:hexanes, 1:10) afforded stannane Compound 33 (200 mg, 83% yield) as a white oil.

Compound 33: $R_f$=0.75 (silica gel, EtOAc:hexanes, 1:5); IR (film) $u_{max}$ 2954, 2923, 2859, 2851, 1456, 1396, 1374, 1312, 1180, 1079, 961, 728, 693, 666, 600, 518 cm$^{-1}$; $^1$H NMR (400 MHz, CDCl₃) δ=3.59 (s, 3 H), 2.61 (s, 3 H), 2.17 (s, 3 H), 1.68-1.45 (m, 6 H), 1.39-1.27 (m, 6 H), 1.20-1.00 (m, 6H), 0.88 ppm (t, J=7.3 Hz, 9 H); $^{13}$C NMR (100 MHz, CDCl$_3$) δ=150.1, 147.0, 133.3, 30.6, 29.1, 27.4, 21.5, 15.8, 13.7, 10.2 ppm; HRMS (ESI-TOF) calcd for C$_{18}$H$_{36}$N$_2$S$_2$Sn$^+$ [M+H$^+$] 465.1415, found 465.1412.

Syndone Compound 34a:

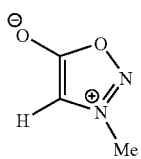

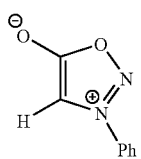

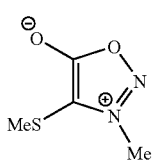

Syndone Compounds 34a, 34b and 34c were prepared according to literature procedure. [Thoman et al. *Org. Synth. Coll.* Vol. V, 962.]

Stannane Compound 35a:

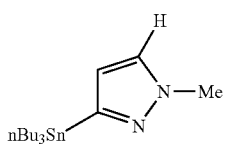

A solution of syndone Compound 34a (6.0 g, 6.0 mmol, 1.0 equiv.) and ethynyl tri-n-butyl tin (2.83 g, 9.0 mmol, 1.5 equiv.) in mixed xylenes (5 mL) was heated to 138° C. for 7 hours. The reaction was cooled to 25° C., diluted with toluene (20 mL) and washed with H$_2$O (2×15 mL) and brine (15 mL), and the organic layer was concentrated in vacuo. Purification of the residue by flash column chromatography (NEt$_3$ prewashed silica gel, EtOAc:hexanes, 1:10) afforded stannane Compound 35a (924 mg, 41% yield) as a colorless oil.

Compound 35a: R$_f$=0.55 (silica gel, EtOAc:hexanes, 1:5); IR (film) u$_{max}$ 2956, 2926, 2871, 2852, 1491, 1463, 1416, 1376, 1338, 1292, 1145, 1071, 874, 751, 688 cm$^{-1}$; $^1$H NMR (600 MHz, CDCl$_3$) δ=7.41 (d, J=1.4 Hz, 1 H), 6.32 (d, J=0.7 Hz, 1 H), 3.95 (s, 3 H), 1.64-1.49 (m, 6 H), 1.39-1.27 (m, 6 H), 1.15-1.03 (m, 6 H), 0.89 ppm (t, J=7.3 Hz, 9 H); $^{13}$C NMR (150 MHz, CDCl$_3$) δ=151.9, 129.6, 113.9, 38.3, 29.0, 27.2, 13.6, 9.7 ppm; HRMS (ESI-TOF) calcd for C$_{16}$H$_{32}$N$_2$Sn$^+$ [M+H$^+$] 373.1660, found 373.1658.

Stannane Compound 35c:

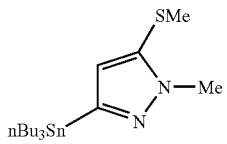

A solution of syndone Compound 34c (1.65 g, 11.3 mmol, 1.0 equiv.) and ethynyl tri-n-butyl tin (5.31 g, 16.9 mmol, 1.5 equiv.) in xylenes (30 mL) was heated to 138° C. for 5 hours. The reaction was cooled to 25° C., diluted with toluene (50 mL) and washed with H$_2$O (2×35 mL) and brine (35 mL), and the organic layer was concentrated in vacuo. Purification of the residue by flash column chromatography (NEt$_3$ prewashed silica gel, EtOAc:hexanes, 1:5) afforded stannane Compound 35c (1.42 g, 30% yield) as a colorless oil.

Compound 35c: R$_f$=0.53 (silica gel, EtOAc:hexanes, 1:10); IR (film) u$_{max}$ 2955, 2924, 2870, 2852, 1454, 1378, 1330, 1286, 1072, 957, 874, 799 cm$^{-1}$; $^1$H NMR (400 MHz, CDCl$_3$) δ=6.30 (s, 1 H), 3.90 (s, 3 H), 2.38 (s, 3 H), 1.66-1.44 (m, 6 H), 1.38-1.27 (m, 6 H), 1.16-0.96 (m, 6 H), 0.88 ppm (t, J=7.3 Hz, 9 H); $^{13}$C NMR (100 MHz, CDCl$_3$) δ=151.8, 135.6, 116.8, 36.3, 29.0, 27.2, 18.7, 13.6, 9.8 ppm; HRMS (ESI-TOF) calcd for C$_{17}$H$_{34}$N$_2$SSn$^+$ [M+H$^+$] 419.1537, found 419.1532.

Stannane Compound 37a:

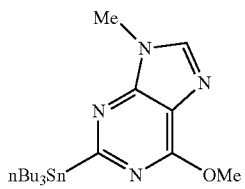

A solution of chloropurine Compound 36 (1.12 g, 2.46 mmol, 1.0 equiv.) and t-BuOK (303 mg, 2.70 mmol, 1.1 equiv.) in MeOH (20 mL) was stirred at 25° C. for 10 minutes. The reaction was concentrated in vacuo and reconstituted with EtOAc (30 mL). The solids were filtered and washed with EtOAc (3×10 mL). The combined organic layers were concentrated in vacuo. Purification of the residue by flash column chromatography (NEt$_3$ prewashed silica gel, EtOAc: hexanes, 1:3→1:1) afforded stannane Compound 37a (113 mg, 10% yield) as a colorless oil.

Compound 37a: R$_f$=0.55 (silica gel, EtOAc:hexanes, 1:1); IR (film) u$_{max}$ 2954, 2926, 2869, 2852, 1591, 1561, 1455, 1375, 1338, 1310, 1215, 1069, 668, 617 cm$^{-1}$; $^1$H NMR (400 MHz, CDCl$_3$) δ=7.78 (s, 1H), 4.13 (s, 3 H), 3.84 (s, 3 H), 1.74-1.50 (m, 6H), 1.40-1.28 (m, 6 H), 1.24-1.05 (m, 6 H), 0.86 ppm (t, J=7.3 Hz, 9 H); $^{13}$C NMR (100 MHz, CDCl$_3$) δ=180.2, 158.3, 151.8, 141.3, 120.1, 53.5, 29.7, 28.9, 27.2, 13.7, 10.5 ppm; HRMS (ESI-TOF) calcd for C$_{19}$H$_{34}$N$_4$OSn$^+$ [M+H$^+$] 455.1827, found 455.1826.

Stannane Compound 37b:

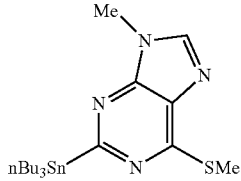

A solution of chloropurine Compound 36 (84 mg, 0.18 mmol, 1.0 equiv.), NaSMe (129 mg, 1.84 mmol, 10.0 equiv.) and t-BuOK (21 mg, 0.18 mmol, 1.0 equiv.) in i-PrOH (1 mL) was stirred at 25 C for 15 minutes. The reaction was concentrated in vacuo and reconstituted with EtOAc (30 mL). The solids were filtered and washed with EtOAc (3×10 mL). The combined organic layers were concentrated in vacuo. Purification of the residue by flash column chromatography (Florisil™, EtOAc:hexanes, 1:3→1:1) afforded stannane Compound 37b (77 mg, 89% yield) as a yellow oil.

Compound 37b: $R_f$=0.55 (silica gel, EtOAc:hexanes 1:1); IR (film) $u_{max}$ 2955, 2927, 2852, 1548, 1463, 1396, 1326, 1261, 1187, 1146, 942, 861, 756, 636 cm$^{-1}$; $^1$H NMR (500 MHz, CDCl$_3$) δ=7.83 (s, 1H), 3.85 (s, 3 H), 2.70 (s, 3 H), 1.73-1.54 (m, 6H), 1.41-1.31 (m, 6 H), 1.27-1.09 (m, 6 H), 0.89 ppm (t, J=7.3 Hz, 9 H); $^{13}$C NMR (125 MHz, CDCl$_3$) δ=180.0, 158.1, 147.9, 141.7, 130.1, 29.6, 29.0, 27.3, 13.7, 11.4, 10.6 ppm; HRMS (ESI-TOF) calcd for C$_{19}$H$_{34}$N$_4$SSn$^+$ [M+H$^+$] 471.1599, found 471.1596.

Each of the patents and articles cited herein is incorporated by reference. The use of the article "a" or "an" is intended to include one or more.

The foregoing description and the examples are intended as illustrative and are not to be taken as limiting. Still other variations within the spirit and scope of this invention are possible and will readily present themselves to those skilled in the art.

What is claimed:

1. A compound that corresponds in structure to Formula A-1, A-2, A-3 or A-4

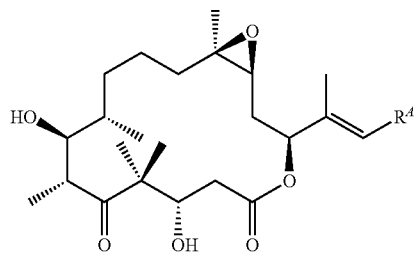

A-1

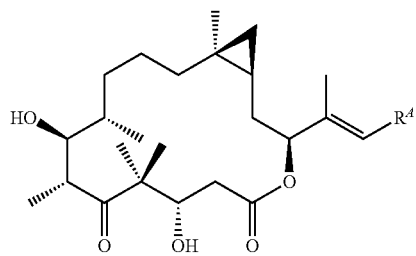

A-2

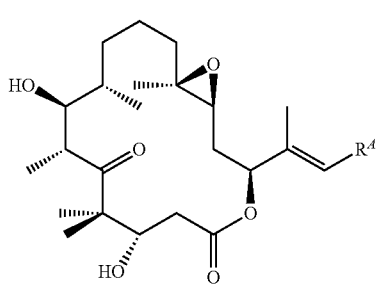

A-3

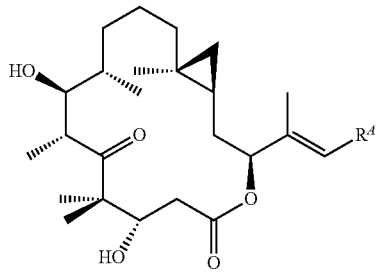

A-4 wherein $R^A$ is an aromatic ring having the structure

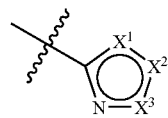

wherein the depicted five-membered ring is aromatic and contains at least two ring atoms that are other than carbon, each of $X^1$, $X^2$ and $X^3$ is independently S, NR$^1$, N, CH, or CR$^2$, $R^1$ is C$_1$-C$_8$-hydrocarbyl or methylene-C$_1$-C$_8$-hydrocarbylether, and $R^2$ is selected from the group consisting of C$_1$-C$_8$-hydrocarbyl, O—C$_1$-C$_8$-hydrocarbyl, halo, S—C$_1$-C$_8$-hydrocarbyl, methylenethio-C$_1$-C$_8$-hydrocarbyl and methylenethio-C$_1$-C$_8$-acyl, with the proviso that when $X^2$ is S and $X^3$ is CR$^2$, R$^2$ is other than C$_1$-C$_8$-hydrocarbyl, O—C$_1$-C$_8$-hydrocarbyl or S—C$_1$-C$_8$-hydrocarbyl; when $X^1$ is CH and $X^2$ is NR$^1$, $X^3$ is other than CH or CR$^2$; when $X^1$ is NR$^1$ and $X^2$ is CH, $X^3$ is other than CR$^2$; when $X^1$ is CH and $X^2$ is N, $X^3$ is other than CH or CR$^2$ wherein $R^2$ is CH$_3$.

2. The compound according to claim 1 wherein $X^1$ is CH.
3. The compound according to claim 1 wherein $X^1$ is N.
4. The compound according to claim 1 wherein $X^1$ is NR$^1$.
5. The compound according to claim 1 wherein $X^1$ is CR$^2$.
6. The compound according to claim 1 wherein $X^1$ is S.
7. The compound according to claim 1 wherein $X^2$ is S.
8. The compound according to claim 1 wherein $X^2$ is NR$^1$.
9. The compound according to claim 1 wherein $X^2$ is N.
10. The compound according to claim 1 wherein $X^2$ is CR$^2$.
11. The compound according to claim 1 wherein $X^3$ is CR$^2$.
12. The compound according to claim 1 wherein $X^3$ is CH.
13. The compound according to claim 1 wherein $X^3$ is NR$^1$.
14. The compound according to claim 1 wherein $R^1$ is C$_1$-C$_8$-hydrocarbyl.
15. The compound according to claim 1 wherein $R^2$ is C$_1$-C$_8$-hydrocarbyl.
16. The compound according to claim 1 wherein $R^2$ is halo.
17. The compound according to claim 1 wherein $R^A$ is

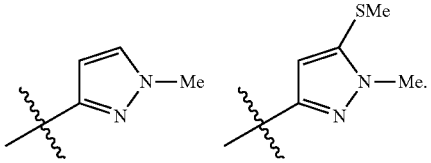

18. The compound according to claim 1 that corresponds in structure to Formula A-1.
19. A compound that corresponds in structure to Formula C-1, C-2, C-3 or C-4

C-1

C-2

C-3

C-4

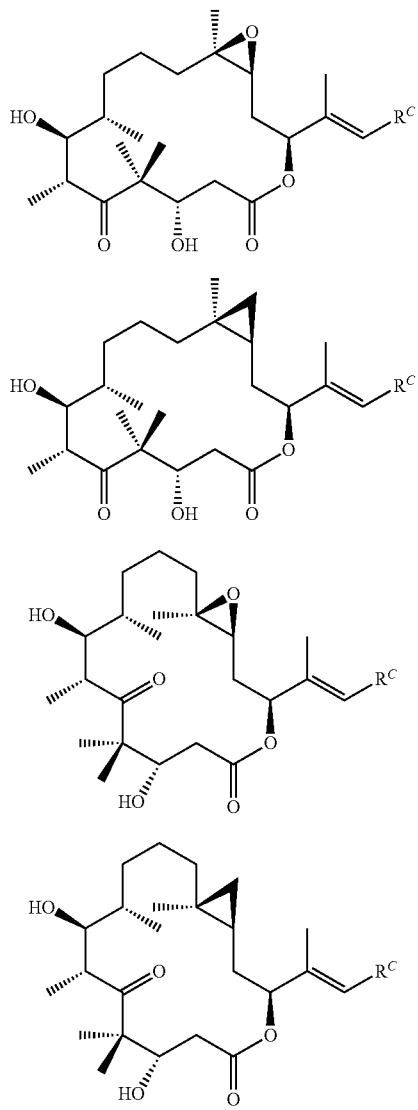

wherein $R^C$ is an aromatic ring having a structure selected from the group consisting of

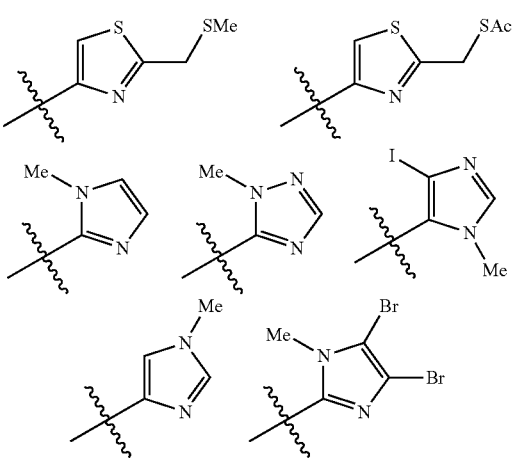

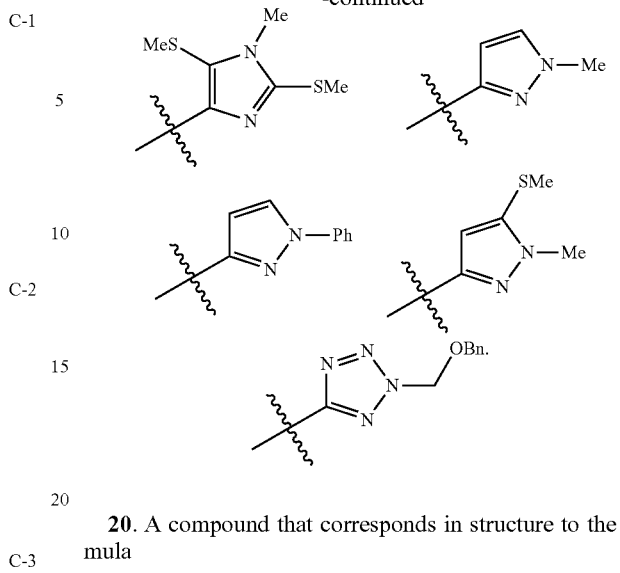

20. A compound that corresponds in structure to the formula

21. A compound that corresponds in structure to the formula

22. A composition containing a pharmaceutically effective amount of a compound of claim 1 dissolved or dispersed in a pharmaceutically acceptable diluent.

23. The composition according to claim 22 wherein $R^A$ is

24. A pharmaceutical composition comprising a compound according to claim 18 present in an effective amount dissolved or dispersed in a pharmaceutically acceptable diluent.

* * * * *